United States Patent
Fukuda

(10) Patent No.: US 11,925,499 B2
(45) Date of Patent: Mar. 12, 2024

(54) IMAGE INTERPRETATION SUPPORT APPARATUS, AND OPERATION PROGRAM AND OPERATION METHOD THEREOF

(71) Applicant: FUJIFILM CORPORATION, Tokyo (JP)

(72) Inventor: Wataru Fukuda, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 477 days.

(21) Appl. No.: 17/209,240

(22) Filed: Mar. 23, 2021

(65) Prior Publication Data

US 2021/0204897 A1 Jul. 8, 2021

Related U.S. Application Data

(63) Continuation of application No. PCT/JP2019/026369, filed on Jul. 2, 2019.

(30) Foreign Application Priority Data

Sep. 28, 2018 (JP) .................. 2018-184403

(51) Int. Cl.
   *G06K 9/00* (2022.01)
   *A61B 6/00* (2006.01)
   (Continued)

(52) U.S. Cl.
   CPC ............ *A61B 6/5211* (2013.01); *A61B 6/025* (2013.01); *A61B 6/502* (2013.01); *A61B 6/54* (2013.01);
   (Continued)

(58) Field of Classification Search
   CPC .......................................... G06T 2207/30068
   See application file for complete search history.

(56) References Cited

U.S. PATENT DOCUMENTS

2004/0223658 A1 11/2004 Shinbata et al.
2007/0297657 A1* 12/2007 Mattes .................... G06T 19/00
                                                   382/128

(Continued)

FOREIGN PATENT DOCUMENTS

JP      2000-276605 A    10/2000
JP       2008-68032 A     3/2008
(Continued)

OTHER PUBLICATIONS

Extended European Search Report dated Oct. 18, 2021, issued in corresponding EP Patent Application No. 19864926.1.
(Continued)

*Primary Examiner* — Hadi Akhavannik
(74) *Attorney, Agent, or Firm* — SOLARIS Intellectual Property Group, PLLC

(57) ABSTRACT

An image interpretation support apparatus includes an acquisition unit, an acceptance unit, and a specifying unit. The acquisition unit acquires a two-dimensional standard image having information on a breast, and a plurality of tomographic images in a plurality of tomographic planes of the breast which are obtained by tomosynthesis imaging of the breast. The acceptance unit accepts a selection instruction of a location on the two-dimensional standard image. In a case where the selection instruction is accepted in the acceptance unit, the specifying unit specifies a corresponding tomographic plane corresponding to a selected location which is the location of which the selection instruction is accepted in the acceptance unit, from among the plurality of tomographic planes on the basis of the plurality of tomographic images.

7 Claims, 20 Drawing Sheets

(51) Int. Cl.

| | |
|---|---|
| *A61B 6/02* | (2006.01) |
| *G06F 3/14* | (2006.01) |
| *G06T 5/00* | (2006.01) |
| *G06T 5/50* | (2006.01) |
| *G06T 7/00* | (2017.01) |
| *G06T 7/70* | (2017.01) |
| *G06T 11/00* | (2006.01) |

(52) U.S. Cl.
CPC ............... *G06F 3/14* (2013.01); *G06T 5/002* (2013.01); *G06T 5/50* (2013.01); *G06T 7/0012* (2013.01); *G06T 7/70* (2017.01); *G06T 11/008* (2013.01); *A61B 6/461* (2013.01); *A61B 6/469* (2013.01); *G06T 2207/10112* (2013.01); *G06T 2207/20221* (2013.01); *G06T 2207/30068* (2013.01); *G06T 2207/30096* (2013.01)

(56) References Cited

U.S. PATENT DOCUMENTS

| | | | |
|---|---|---|---|
| 2008/0152086 A1 | 6/2008 | Hall et al. | |
| 2012/0071756 A1* | 3/2012 | Yu ..................... | A61B 8/5215 600/437 |
| 2012/0300899 A1 | 11/2012 | Tajima et al. | |
| 2015/0269766 A1* | 9/2015 | Kobayashi ............ | A61B 6/469 345/419 |
| 2016/0095563 A1 | 4/2016 | Fukuda et al. | |
| 2017/0053403 A1 | 2/2017 | Fieselmann | |

FOREIGN PATENT DOCUMENTS

| | | |
|---|---|---|
| JP | 2011-123045 A | 6/2011 |
| JP | 2012-245060 A | 12/2012 |
| JP | 2014-239840 A | 12/2014 |
| JP | 2015-177928 A | 10/2015 |
| WO | 2012/107057 A1 | 8/2012 |
| WO | 2014/203531 A1 | 12/2014 |

OTHER PUBLICATIONS

English language translation of the following: Decision of Refusal dated Jul. 19, 2022 from the JPO in a Japanese patent application No. 2020-548006 corresponding to the instant patent application.
English language translation of the following: Office action dated Apr. 12, 2022 from the JPO in a Japanese patent application No. 2020-548006 corresponding to the instant patent application. This office action translation is submitted now in order to supplement the understanding of the cited references which are being disclosed in the instant Information Disclosure Statement.
International Search Report issued in International Application No. PCT/JP2019/026369 dated Sep. 17, 2019.
Written Opinion of the ISA issued in International Application No. PCT/JP2019/026369 dated Sep. 17, 2019.

* cited by examiner

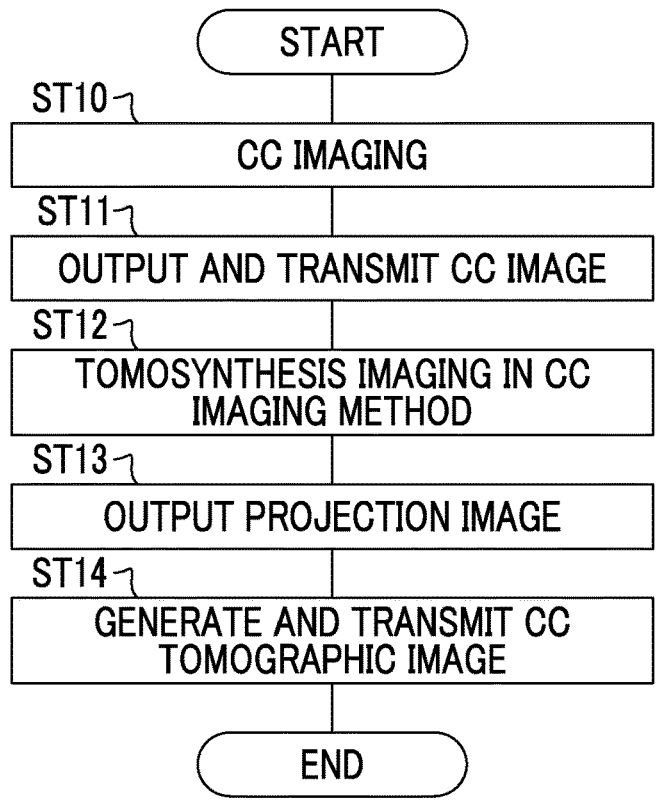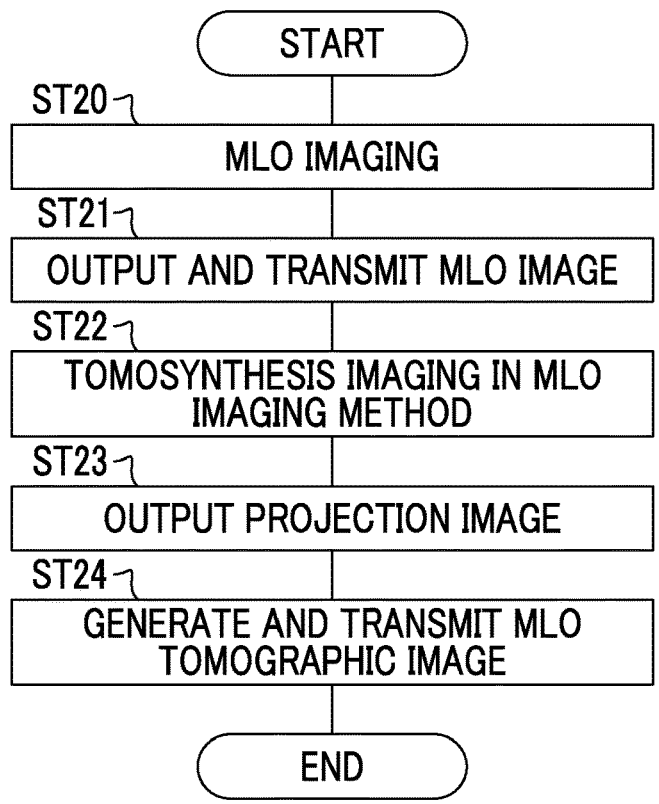

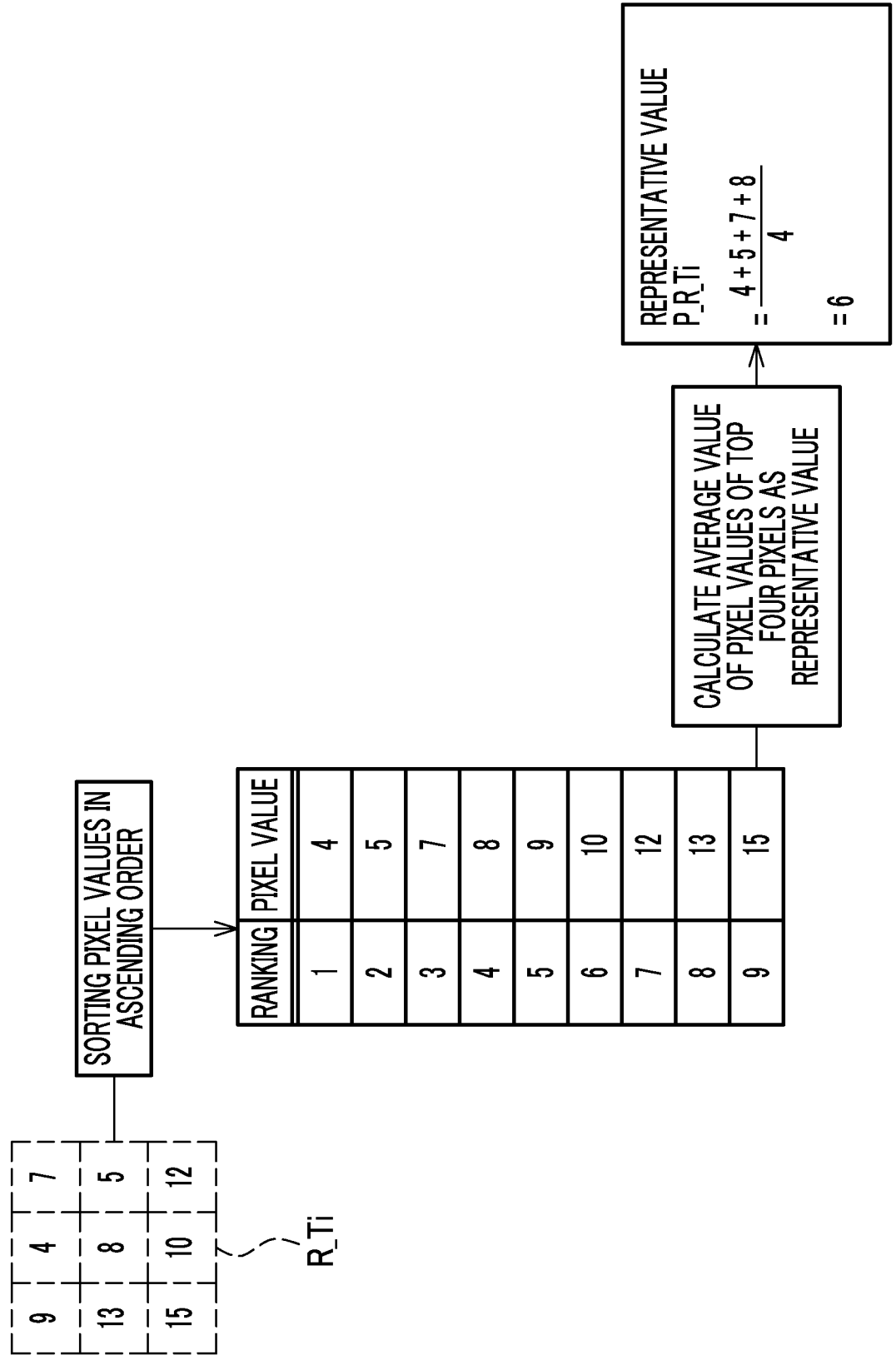

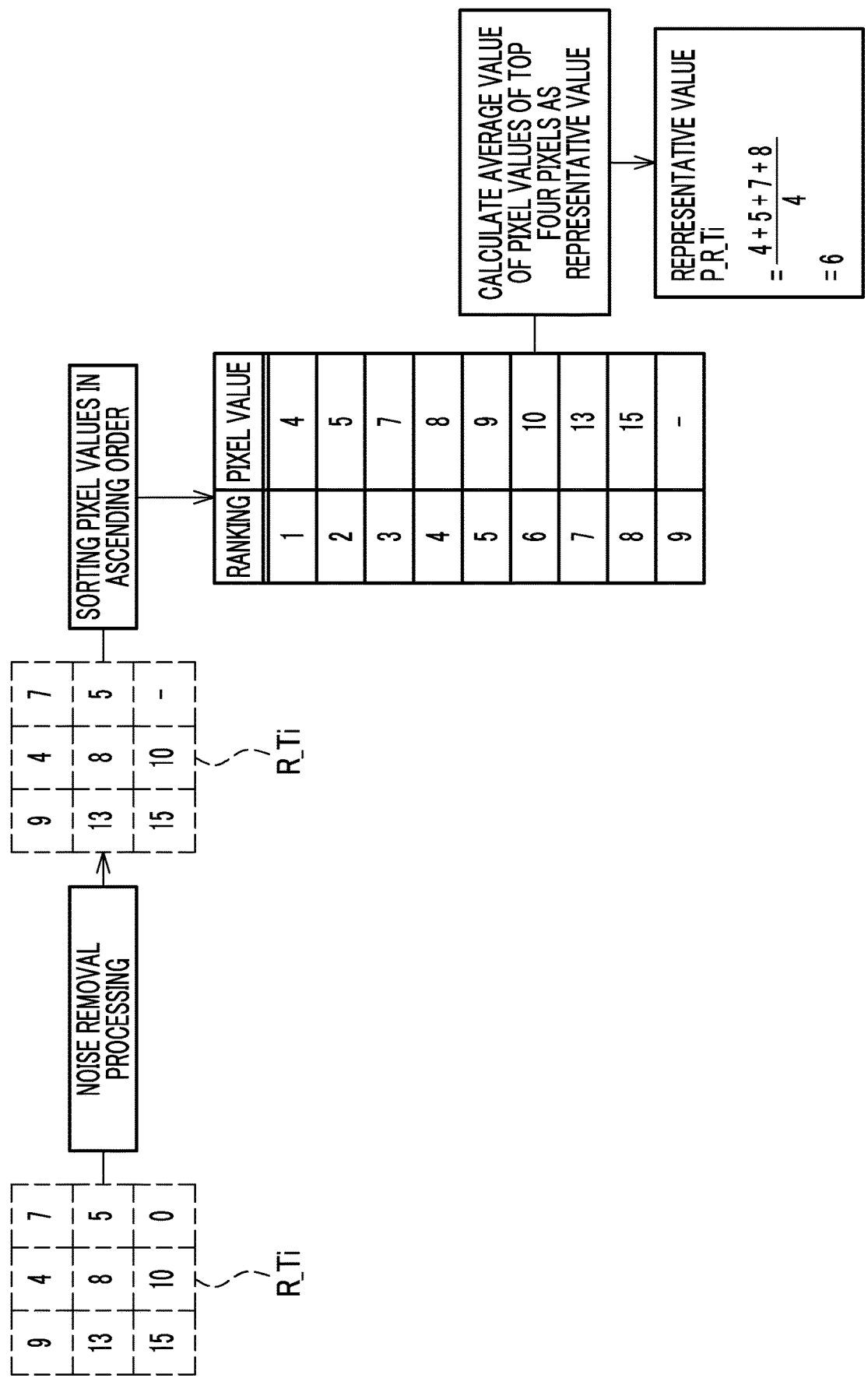

IMAGE INTERPRETATION SUPPORT APPARATUS, AND OPERATION PROGRAM AND OPERATION METHOD THEREOF

CROSS-REFERENCE TO RELATED APPLICATIONS

This application is a continuation application of International Application No. PCT/JP2019/026369 filed Jul. 2, 2019, the disclosure of which is incorporated herein by reference in its entirety. Further, this application claims priority from Japanese Patent Application No. 2018-184403 filed on Sep. 28, 2018, the disclosure of which is incorporated herein by reference in its entirety.

BACKGROUND OF THE INVENTION

1. Technical Field

The technology of the present disclosure relates to an image interpretation support apparatus, and an operation program and an operation method thereof.

2. Description of the Related Art

In a mammography apparatus which images a breast as a subject, tomosynthesis imaging is performed. In the tomosynthesis imaging, a radiation source is moved to a plurality of positions with respect to a radiation detector, and radiation is emitted from the radiation source at each position. Then, a plurality of tomographic images in a plurality of tomographic planes of the breast are generated from a plurality of projection images obtained in this manner.

In the image interpretation, a user such as a radiologist does not immediately interpret a tomographic image, but first interprets a two-dimensional standard image. The user roughly guesses a location of a lesion part such as calcification in the two-dimensional standard image. Then, the user searches for a tomographic image of a tomographic plane where the guessed lesion part is likely to be present, and interprets the searched tomographic image in detail. Such an image interpretation procedure is used because it is inefficient to randomly interpret a plurality of tomographic images without any guess at first.

The two-dimensional standard image is, for example, a simple imaging image obtained by so-called simple imaging in which a radiation source faces a radiation detector (the radiation source is arranged on a normal line passing through the center of a detection surface of the radiation detector to face the detection surface) to emit the radiation. In the simple imaging, there are craniocaudal view (CC) imaging in which the breast is imaged by being vertically sandwiched and pressed, and mediolateral oblique view (MLO) imaging in which the breast is imaged by being obliquely sandwiched at an angle of about 60° and pressed. Hereinafter, the simple imaging image obtained by the CC imaging is referred to as a CC image, and the simple imaging image obtained by the MLO imaging is referred to as an MLO image.

WO2014/203531A discloses a technology to save labor of searching for tomographic images during image interpretation. That is, the two-dimensional standard image is divided into a plurality of regions, and similarly, each tomographic image is divided into a plurality of regions. Then, a correlation between the region of the two-dimensional standard image and the region of each tomographic image is obtained, and a tomographic plane of the tomographic image having the region with the largest correlation is specified as a corresponding tomographic plane which corresponds to the region of the two-dimensional standard image.

More specifically, a correlation between a region R_S of a two-dimensional standard image S and a region R_Ti of each tomographic image Ti (i=1 to N, N is the number of tomographic images) having a positional relationship corresponding thereto. Then, in a case where the region with the largest correlation with the region R_S is, for example, a region R_T10 of a tomographic image T10, a tomographic plane TF10 of the tomographic image T10 is specified as a corresponding tomographic plane of the region R_S. The corresponding tomographic plane is specified for each region. Information on the corresponding tomographic plane specified in this manner and the region of the two-dimensional standard image are stored as correspondence information (indicated as a depth map in WO2014/203531A).

Next, on a display screen of the two-dimensional standard image, a selection instruction of a location on the two-dimensional standard image by the user is accepted. The corresponding tomographic plane of the region in which the location selected by the selection instruction is present is read out from the correspondence information, and the tomographic image of the read corresponding tomographic plane is displayed on the display screen together with the two-dimensional standard image.

SUMMARY

In WO2014/203531A, as described above, the corresponding tomographic plane is specified for each region. However, the information on the corresponding tomographic plane is required only in the region where the location selected by the selection instruction by the user is present. Accordingly, except for the region where the location selected by the selection instruction by the user is present, the processing of specifying the corresponding tomographic plane is useless.

An object of the technology of the present disclosure is to provide an image interpretation support apparatus and an operation program and an operation method thereof which can reduce useless processing.

In order to achieve the above object, an image interpretation support apparatus according to an aspect of the present disclosure comprises an acquisition unit that acquires a two-dimensional standard image having information on a breast, and a plurality of tomographic images in a plurality of tomographic planes of the breast which are obtained by tomosynthesis imaging of the breast; an acceptance unit that accepts a selection instruction of a location on the two-dimensional standard image; and a specifying unit that, in a case where the selection instruction is accepted in the acceptance unit, specifies a corresponding tomographic plane corresponding to a selected location which is the location of which the selection instruction is accepted in the acceptance unit, from among the plurality of tomographic planes on the basis of the plurality of tomographic images.

It is preferable that the image interpretation support apparatus further comprises a display controller that performs control to display the tomographic image of the corresponding tomographic plane specified in the specifying unit, on a display unit.

It is preferable that the display controller performs control to display the two-dimensional standard image on the display unit, in addition to the tomographic image of the corresponding tomographic plane specified in the specifying unit.

It is preferable that the specifying unit specifies the tomographic plane corresponding to a region composed of a pixel of the selected location and a plurality of pixels around the pixel of the selected location, as the corresponding tomographic plane corresponding to the selected location.

It is preferable that the specifying unit obtains a representative value of pixel values of a region of the tomographic image having a positional relationship corresponding to the region, and specifies the corresponding tomographic plane on the basis of the representative value.

It is preferable that, in a case where the pixel values of the pixels of the region of the tomographic image are sorted in an ascending order, the representative value is an average value of the pixel values of the pixels from a preset higher rank to a preset lower rank, or in a case where the pixel values of the pixels of the region of the tomographic image are sorted in a descending order, the representative value is an average value of the pixel values of the pixels from a preset higher rank to a preset lower rank.

It is preferable that the specifying unit obtains the representative value after noise removal processing is performed on the region of the tomographic image.

It is preferable that the two-dimensional standard image is at least one of a craniocaudal view image obtained by imaging the breast in a craniocaudal direction, a mediolateral oblique view image obtained by imaging the breast in a mediolateral oblique direction, a composite craniocaudal view image generated on the basis of a plurality of craniocaudal view tomographic images obtained by the tomosynthesis imaging of the breast in a craniocaudal view imaging method, or a composite mediolateral oblique view image generated on the basis of a plurality of mediolateral oblique view tomographic images obtained by the tomosynthesis imaging of the breast in a mediolateral oblique view imaging method.

An operation program of an image interpretation support apparatus according to another aspect of the present disclosure causes a computer to function as: an acquisition unit that acquires a two-dimensional standard image having information on a breast, and a plurality of tomographic images in a plurality of tomographic planes of the breast which are obtained by tomosynthesis imaging of the breast; an acceptance unit that accepts a selection instruction of a location on the two-dimensional standard image; and a specifying unit that, in a case where the selection instruction is accepted in the acceptance unit, specifies a corresponding tomographic plane corresponding to a selected location which is the location of which the selection instruction is accepted in the acceptance unit, from among the plurality of tomographic planes on the basis of the plurality of tomographic images.

An operation method of an image interpretation support apparatus according to still another aspect of the present disclosure comprises an acquisition step of acquiring a two-dimensional standard image having information on a breast, and a plurality of tomographic images in a plurality of tomographic planes of the breast which are obtained by tomosynthesis imaging of the breast; an acceptance step of accepting a selection instruction of a location on the two-dimensional standard image; and a specifying step of, in a case where the selection instruction is accepted in the acceptance step, specifying a corresponding tomographic plane corresponding to a selected location which is the location of which the selection instruction is accepted in the acceptance step, from among the plurality of tomographic planes on the basis of the plurality of tomographic images.

According to the technology of the present disclosure, it is possible to provide an image interpretation support apparatus and an operation program and an operation method thereof which can reduce useless processing.

BRIEF DESCRIPTION OF THE DRAWINGS

Exemplary embodiments according to the technique of the present disclosure will be described in detail based on the following figures, wherein:

FIG. 6 is a flowchart illustrating a procedure of imaging a breast by a mammography apparatus;
FIG. 7 is a flowchart illustrating a procedure of imaging the breast by the mammography apparatus;
FIG. 22 is a diagram illustrating a third embodiment in which, in a case where pixel values of pixels of the region of the tomographic image are sorted in an ascending order, an average value of the pixel values of the pixels from a preset higher rank to a preset lower rank is used as a representative value;
and
FIG. 23 is a diagram illustrating a fourth embodiment in which a representative value is obtained after noise removal processing is performed on the regions of the tomographic image.

DETAILED DESCRIPTION

First Embodiment

Figure 1:
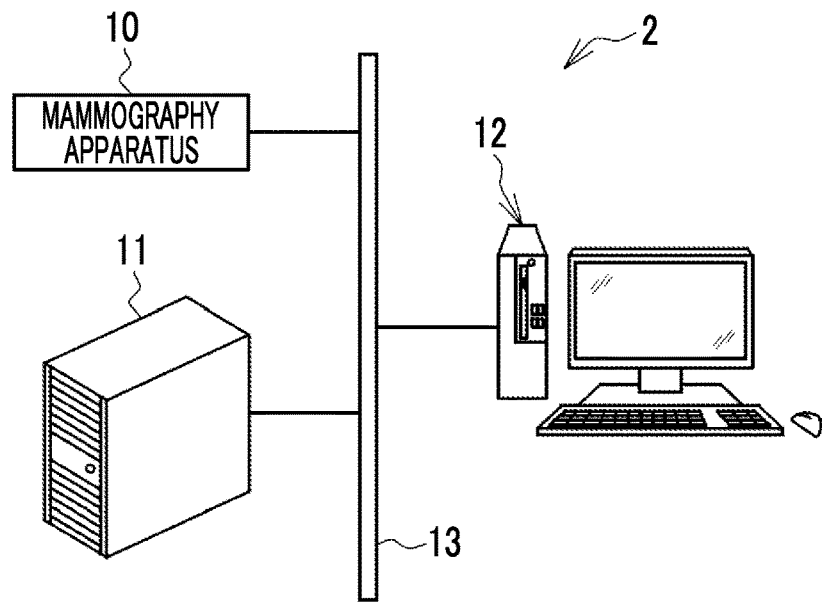
FIG. 1 is a diagram illustrating a medical system.

In FIG. 1, a medical system 2 comprises a mammography apparatus 10, a picture archiving and communication system (PACS) server 11, and an image interpretation support apparatus 12, and is installed at one medical facility, for example. As is well known, the mammography apparatus 10 emits radiation 24 (refer to FIG. 2 or the like) to a breast 23 (refer to FIG. 2, or the like), and outputs a radiographic image of the breast 23. The radiation 24 is, for example, X-rays (y-rays are also possible). As is also well known, the PACS server 11 stores the radiographic image output from the mammography apparatus 10, and transmits the radiographic image to the image interpretation support apparatus 12. The image interpretation support apparatus 12 is operated by the user such as a radiologist. The mammography apparatus 10, the PACS server 11, and the image interpretation support apparatus 12 are connected so as to communicate with each other via a network 13 such as a local area network (LAN).

The PACS server 11 and the image interpretation support apparatus 12 are based on a computer such as a server computer, a workstation, or a personal computer. The PACS server 11 and the image interpretation support apparatus 12 are configured by installing a control program such as an operating system and various application programs on such a computer.

Figure 2:
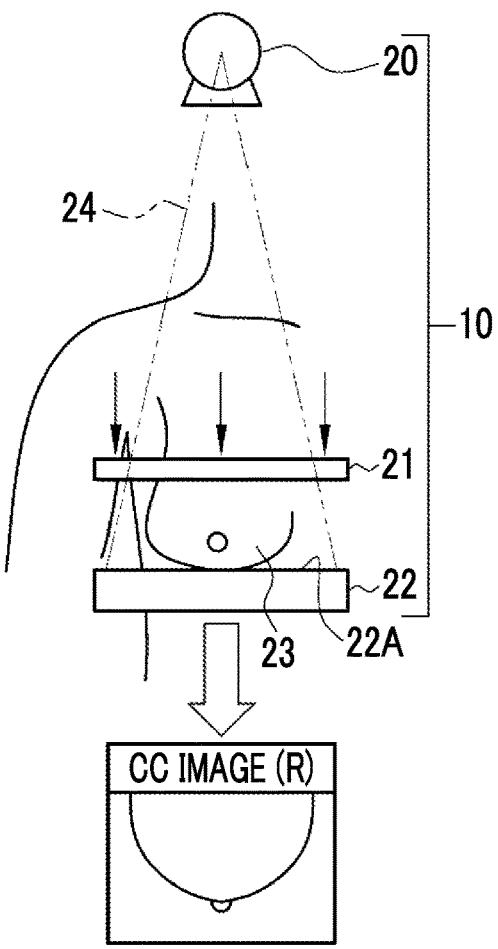
FIG. 2 is a diagram illustrating a state of CC imaging.
Figure 3:
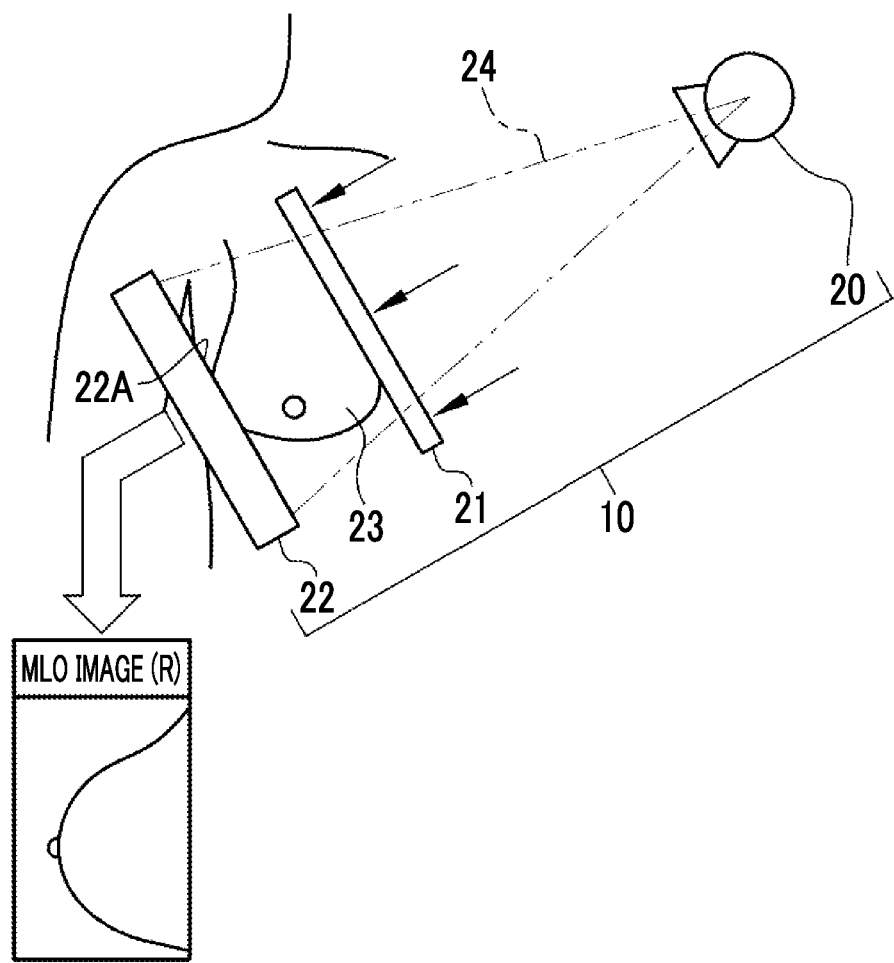
FIG. 3 is a diagram illustrating a state of MLO imaging.

In FIGS. 2 and 3, the mammography apparatus 10 has a radiation source 20, a pressing plate 21, and a radiation detector 22. The radiation source 20 emits the radiation 24 to the breast 23 as indicated by two-dot chain lines. The pressing plate 21 is formed of a material that transmits the radiation 24. The pressing plate 21 pushes down the breast 23 in a vertical direction illustrated in FIG. 2 or in an obliquely downward direction illustrated in FIG. 3. The radiation detector 22 faces the pressing plate 21, and presses the breast 23 by vertically sandwiching the breast 23 with the pressing plate 21 (FIG. 2) or presses the breast 23 by obliquely sandwiching the breast 23 at an angle of about 60° with the pressing plate 21 (FIG. 3). The radiation detector 22 detects the radiation 24 that is emitted from the radiation source 20 and is transmitted through the pressing plate 21 and the breast 23, and outputs a radiographic image. The radiographic image output from the radiation detector 22 is transmitted to the PACS server 11 and is stored in the PACS server 11.

FIG. 2 illustrates a state of CC imaging in which the breast 23 is imaged by being vertically sandwiched and pressed, and which is simple imaging in which the radiation source 20 faces the radiation detector 22 (the radiation source 20 is arranged on a normal line passing through the center of a detection surface 22A of the radiation detector 22 to face the detection surface 22A) to emit the radiation 24. In this case, the radiation detector 22 outputs a CC image as the radiographic image. On the other hand, FIG. 3 illustrates a state of MLO imaging in which the breast 23 is imaged by being obliquely sandwiched and pressed, and which is also simple imaging. In this case, the radiation detector 22 outputs an MLO image as the radiographic image. Although FIGS. 2 and 3 illustrate the CC imaging and the MLO imaging for the right breast 23, the CC imaging and the MLO imaging are similarly performed for the left breast 23.

Figure 4:
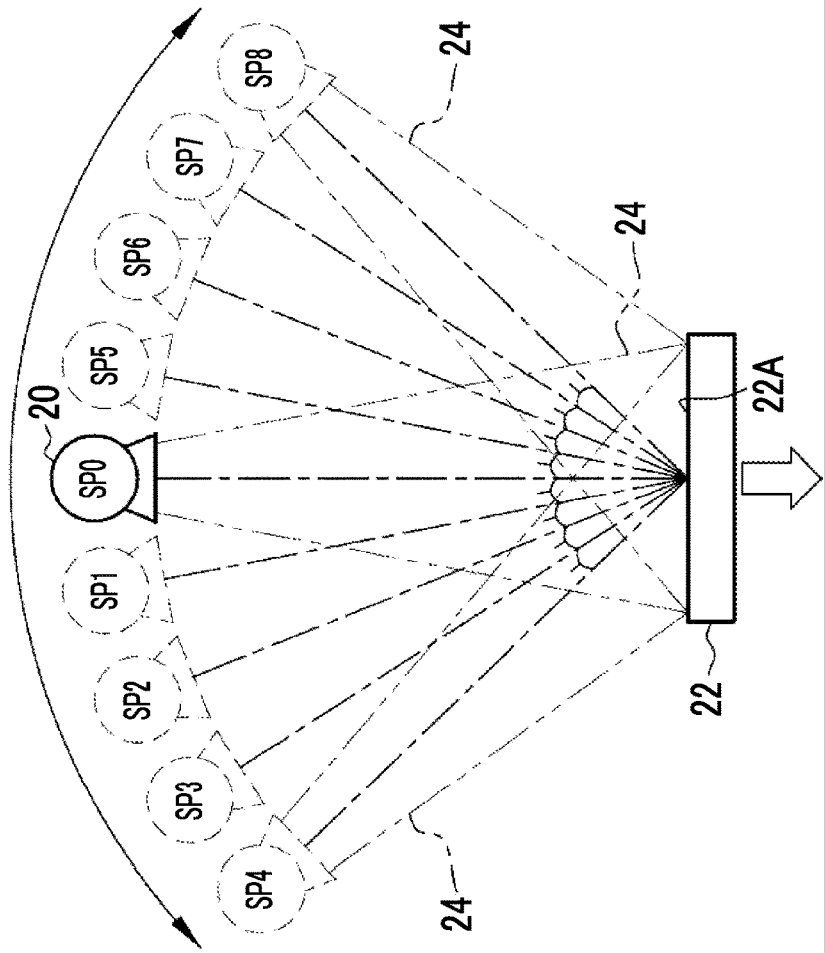
FIG. 4 is a diagram illustrating a state of tomosynthesis imaging.

In FIG. 4 which conceptually illustrates a state of tomosynthesis imaging, the radiation source 20 is sequentially moved to a total of nine positions SP0 to SP8 arranged at equal angles in an arc shape with respect to the radiation detector 22. Then, the radiation 24 (not illustrated except for the positions SP0, SP4, and SP8) is emitted to the breast 23 at each of the positions SP0 to SP8. The radiation detector 22 detects the radiation 24 emitted at each of the positions SP0 to SP8, and outputs a projection image at each of the positions SP0 to SP8 as the radiographic image. The tomosynthesis imaging is performed in both the CC imaging method and the MLO imaging method, and is performed on each of the left and right breasts 23 in each of both the imaging methods. Here, the position SP0 is a position of the simple imaging, at which the radiation source 20 faces the radiation detector 22. The positions of the tomosynthesis imaging are not limited to the above-described nine positions. Further, the movement trajectory of the radiation source 20 is not limited to the above-described arc shape, and may be a linear shape parallel to the detection surface 22A of the radiation detector 22 or an elliptical arc shape.

Figure 5:
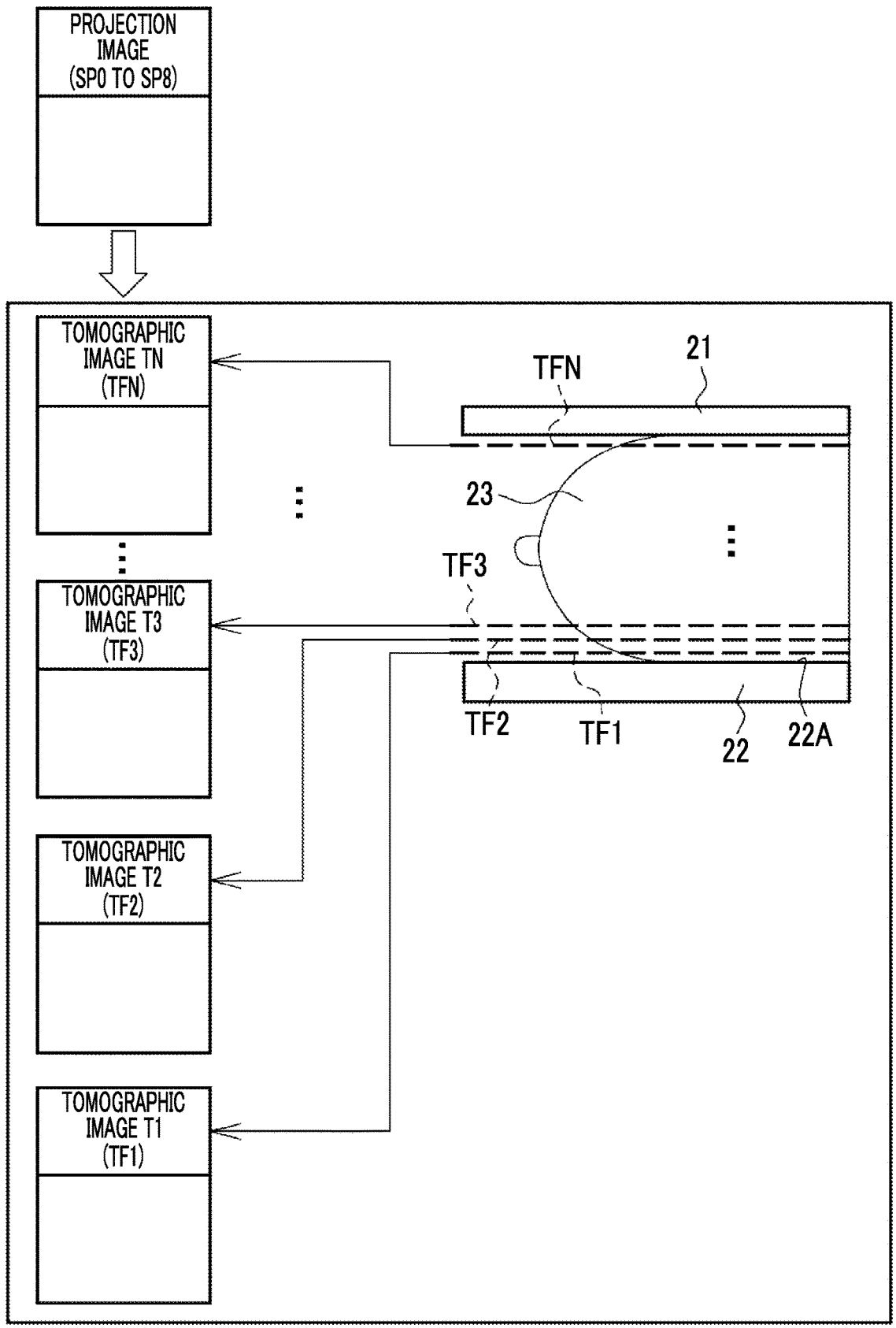
FIG. 5 is a diagram illustrating a state in which a plurality of tomographic images are generated from a plurality of projection images obtained in the tomosynthesis imaging.

As illustrated in FIG. 5, the mammography apparatus 10 generates a plurality of tomographic images $T_i$ ($i=1$ to N, N is the number of tomographic images) from a plurality of projection images obtained by the tomosynthesis imaging illustrated in FIG. 4, by using a well-known method such as a filtered back projection method. The tomographic image $T_i$ is an image in which a structure present in each of a plurality of tomographic planes $TF_i$ of the breast 23 is emphasized. The tomographic images $T_i$ and the tomographic planes $TF_i$ have a one-to-one correspondence. Therefore, the same subscript i is used for the tomographic image $T_i$ and the tomographic plane $TF_i$. Each tomographic image $T_i$ is transmitted to the PACS server 11, and is stored in the PACS server 11 in association with the CC image and the MLO image. In the following, the tomographic image obtained by the tomosynthesis imaging in the CC imaging method is expressed as a CC tomographic image (refer to FIG. 6 or the like), and the tomographic image obtained by the tomosynthesis imaging in the MLO imaging method is expressed as an MLO tomographic image (refer to FIG. 7 or the like).

The tomographic plane $TF_i$ is a plane parallel to the detection surface 22A of the radiation detector 22. An interval between adjacent tomographic planes $TF_i$ is, for example, 1 mm. The tomographic plane $TF_1$ which is closest to the detection surface 22A of the radiation detector 22 is at a height of 10 mm from the detection surface 22A, for example. The tomographic plane $TF_N$ which is farthest from the detection surface 22A (closest to the radiation source 20) is at a height of 60 mm from the detection surface 22A (at a height of 50 mm from the tomographic plane $TF_1$), for example. In this case, $N=51$. The numerical values relating to the tomographic planes $TF_i$ described here are merely examples, and are not limited thereto.

FIGS. 6 and 7 are flowcharts illustrating a procedure of imaging the breast 23 by the mammography apparatus 10. First, as illustrated in FIG. 6, in the mammography apparatus 10, the CC imaging illustrated in FIG. 2 is performed (Step ST10). In this manner, the CC image is output from the radiation detector 22, and is transmitted to the PACS server 11 (Step ST11).

Subsequently, in the mammography apparatus 10, the tomosynthesis imaging illustrated in FIG. 4 is performed in the CC imaging method (Step ST12). In this manner, a plurality of projection images are output from the radiation detector 22 (Step ST13). Then, as illustrated in FIG. 5, a plurality of CC tomographic images are generated from the plurality of projection images, and are transmitted to the PACS server 11 (Step ST14).

Similarly, as illustrated in FIG. 7, in the mammography apparatus 10, the MLO imaging illustrated in FIG. 3 is performed (Step ST20), and the MLO image is output from the radiation detector 22, and is transmitted to the PACS server 11 (Step ST21). Subsequently, the tomosynthesis imaging is performed in the MLO imaging method (Step ST22), the projection image is output (Step ST23), and the MLO tomographic image is generated and is transmitted to the PACS server 11 (Step ST24). These series of imaging procedures are performed on each of the left and right breasts 23. The order of CC imaging and MLO imaging may be reversed.

In the CC imaging and the MLO imaging, a relatively high amount of radiation 24 is emitted. On the other hand, in the tomosynthesis imaging in the CC imaging method and the tomosynthesis imaging in the MLO imaging method, a lower amount of radiation 24 than that in the CC imaging and the MLO imaging is emitted. Further, in the tomosynthesis imaging, the same dose of radiation 24 is emitted at each of the positions SP0 to SP8.

Figure 8:
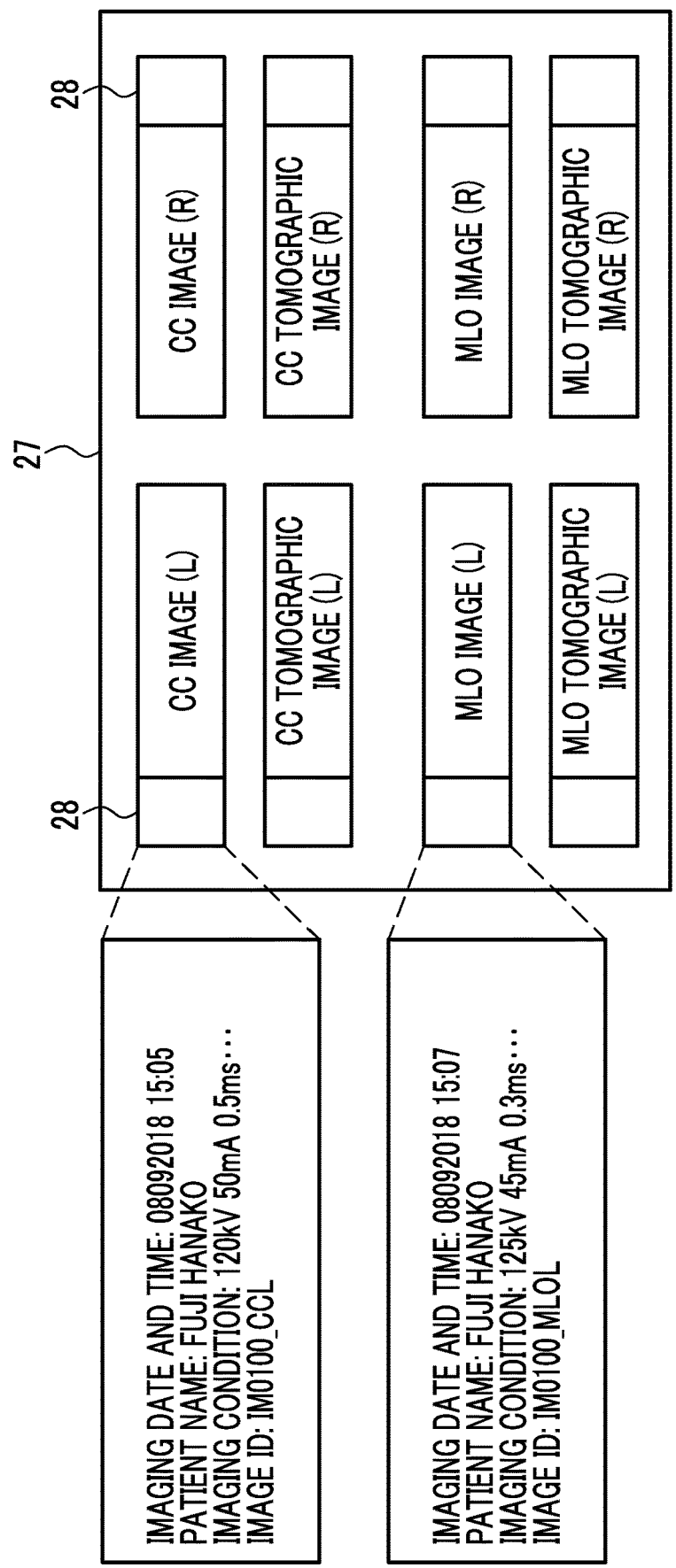
FIG. 8 is a diagram illustrating an image set.

By performing imaging in the imaging procedure illustrated in FIGS. 6 and 7, an image set 27 illustrated in FIG. 8 is stored in the PACS server 11. The image set 27 has a CC image (R) and a CC tomographic image (R) obtained by imaging the right breast 23 in the CC imaging method, and an MLO image (R) and an MLO tomographic image (R) obtained by imaging the right breast 23 in the MLO imaging method. Further, the image set 27 has a CC image (L) and a CC tomographic image (L) obtained by imaging the left breast 23 in the CC imaging method, and an MLO image (L) and an MLO tomographic image (L) obtained by imaging the left breast 23 in the MLO imaging method.

Each image constituting the image set 27 has accessory information 28 such as imaging date and time, a patient name, and an imaging condition. The imaging condition includes a tube voltage (120 kV or the like) applied to the radiation tube of the radiation source 20, a tube current (50 mA or the like), and an irradiation time (0.5 ms or the like) of the radiation 24. The images constituting the image set 27 have a common image identification data (ID) such as IM0100, and are associated with each other. Then, a symbol representing the type of each image, such as CCL of the CC image (L), is added to the common image ID so that the images are distinguished from each other. The image set 27 is transmitted to the image interpretation support apparatus 12. In the following, in a case where it is not necessary to distinguish the images from each other, (R) indicating the image of the right breast 23 and (L) indicating the image of the left breast 23 are not written. In addition to these images, the projection image which is the generation source of the tomographic image may be included in the image set 27. Further, instead of the tube current and the irradiation time, the tube current irradiation time product may be stored as the imaging condition.

In the embodiment, at least one image of the CC image or the MLO image is the two-dimensional standard image which has information on the breast 23 and on which a selection instruction of a location is accepted.

Figure 9:
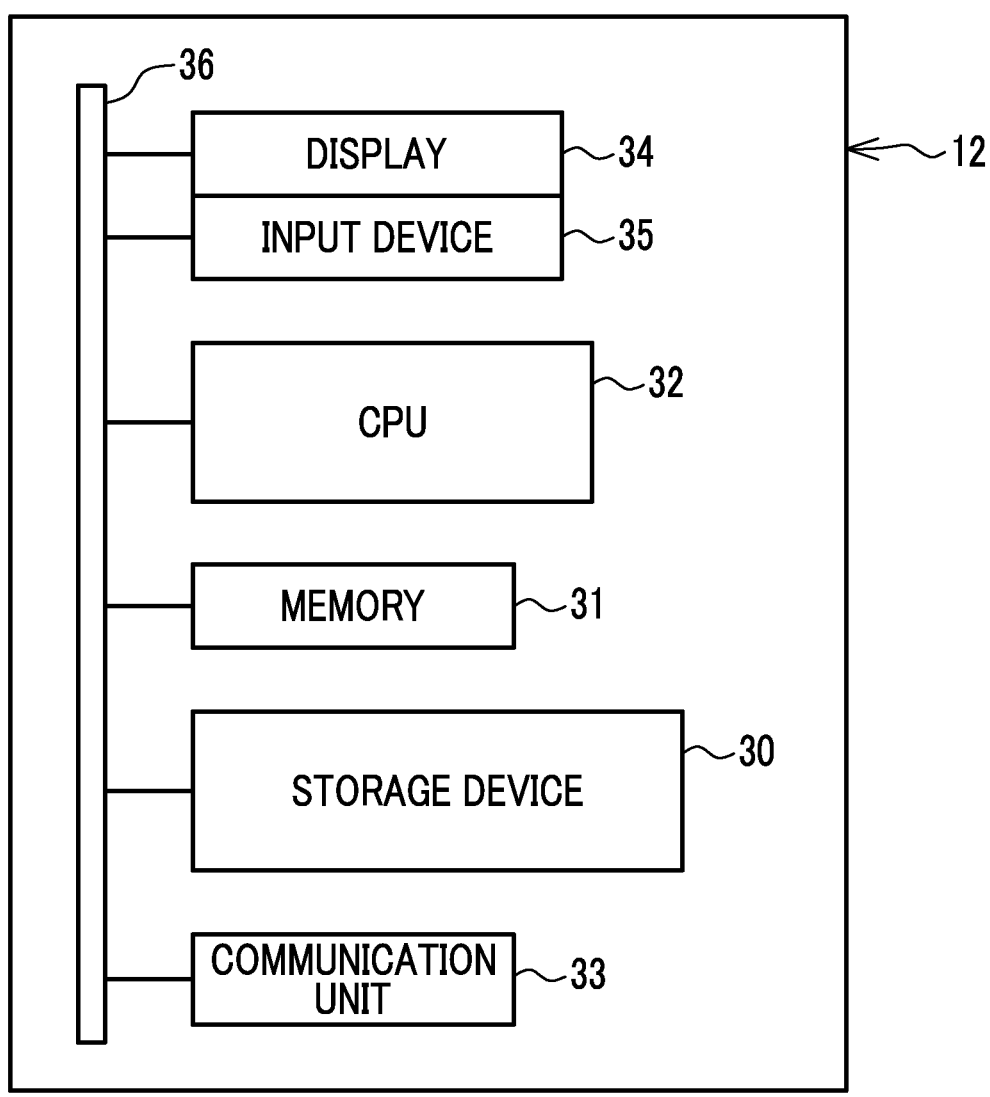
FIG. 9 is a block diagram illustrating a computer constituting an image interpretation support apparatus.

In FIG. 9, the computer constituting the image interpretation support apparatus 12 comprises a storage device 30, a memory 31, a central processing unit (CPU) 32, a communication unit 33, a display 34, and an input device 35. These are connected to each other through a bus line 36.

The storage device 30 is a hard disk drive that is built in the computer constituting the image interpretation support apparatus 12 or is connected to the computer constituting the image interpretation support apparatus 12 through a cable or a network. Alternatively, the storage device 30 is a disk array in which a plurality of hard disk drives are connected. Control programs such as an operating system, various application programs, and various kinds of data associated with these programs are stored in the storage device 30. Instead of the hard disk drive, a solid state drive may be used.

The memory 31 is a work memory required for the CPU 32 to execute processing. The CPU 32 performs overall control of each unit of the computer by loading a program stored in the storage device 30 to the memory 31 and executing the processing according to the program.

The communication unit 33 is a network interface to perform transmission control of various kinds of information through the network 13. The display 34 displays various screens. The various screens comprise operation functions by a graphical user interface (GUI). The computer constituting the image interpretation support apparatus 12 accepts an input of an operation instruction from the input device 35 through the various screens. The input device 35 is a keyboard, a mouse, a touch panel, or the like.

Figure 10:
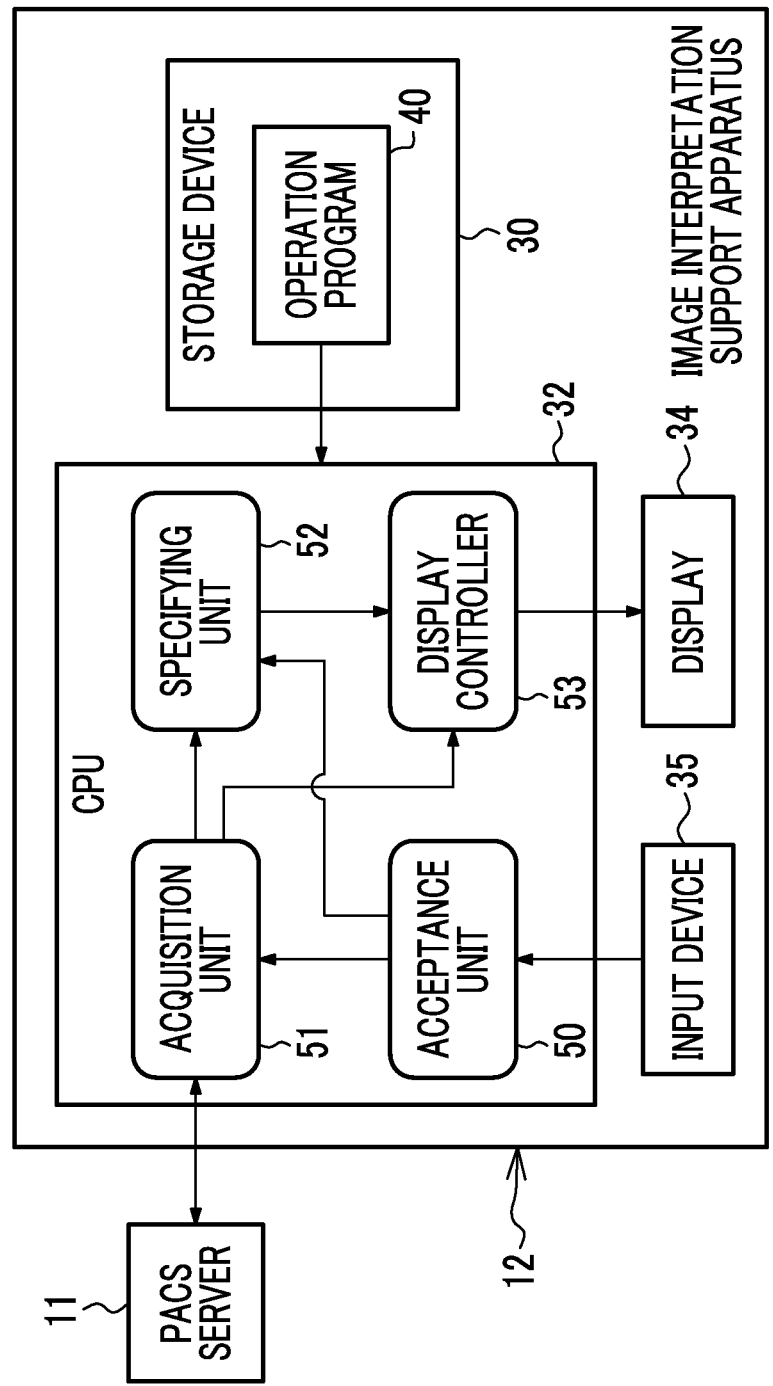
FIG. 10 is a block diagram illustrating a processing unit of a CPU of the image interpretation support apparatus.

In FIG. 10, an operation program 40 is stored as the application program in the storage device 30 of the image interpretation support apparatus 12. The operation program 40 is an application program for causing the computer to function as the image interpretation support apparatus 12. That is, the operation program 40 is an example of an "operation program of the image interpretation support apparatus" according to the technology of the present disclosure.

In a case where the operation program 40 is activated, the CPU 32 of the computer constituting the image interpretation support apparatus 12 cooperates with the memory 31 or the like to function as an acceptance unit 50, an acquisition unit 51, a specifying unit 52, and a display controller 53.

The acceptance unit 50 accepts an operation instruction input from the input device 35 through the various screens displayed on the display 34. As the operation instruction, there are a transmission instruction of the image set 27 to the PACS server 11, a selection instruction of a location on at least one image of the CC image or the MLO image, and the like. In the transmission instruction, information (image ID, patient name, imaging date and time, and the like) for uniquely identifying the image set 27 is included. In the selection instruction, positional information on the location which is selected by the selection instruction (hereinafter, referred to as a selected location) is included. The positional information is, for example, XY coordinates in a case where a pixel on the left end of the image is set as the origin, the horizontal side of the image is set as an X axis, and the vertical side is set as a Y axis, and is XY coordinates of a pixel 60A (refer to FIG. 11) corresponding to the selected location. The acceptance unit 50 outputs the transmission instruction to the acquisition unit 51, and outputs the selection instruction to the specifying unit 52.

The acquisition unit 51 issues a transmission request for the image set 27 according to the transmission instruction from the acceptance unit 50, to the PACS server 11. In the transmission request, as in the transmission instruction, information for uniquely identifying the image set 27 is included. The acquisition unit 51 acquires the image set 27 transmitted from the PACS server 11 in response to the transmission request. As illustrated in FIG. 8, in the image set 27, the CC image and the MLO image which are the two-dimensional standard images, the CC tomographic image, and the MLO tomographic image are included. Accordingly, the acquisition unit 51 acquires the two-dimensional standard image and the tomographic image by acquiring the image set 27. The acquisition unit 51 outputs the acquired image set 27 to the specifying unit 52 and the display controller 53.

The specifying unit 52 specifies a CC corresponding tomographic plane on the basis of the plurality of CC tomographic images of the image set 27 from the acquisition unit 51. Further, the specifying unit 52 specifies an MLO corresponding tomographic plane on the basis of the plurality of MLO tomographic images of the image set 27 from the acquisition unit 51. Here, the CC corresponding tomographic plane is a tomographic plane corresponding to the selected location of the CC image. More specifically, the CC corresponding tomographic plane is a tomographic plane where a structure shown in the selected location of the CC image is present. Similarly, the MLO corresponding tomographic plane is a tomographic plane corresponding to the selected location of the MLO image, and is a tomographic plane where a structure shown in the selected location of the MLO image is present. The specifying unit 52 specifies one tomographic plane among the plurality of tomographic planes TFi of the breast 23 illustrated in FIG. 5, as the corresponding tomographic plane, for the selected location of the CC image. Similarly, the specifying unit 52 specifies one corresponding tomographic plane for the selected location of the MLO image. The specifying unit 52 outputs information on the specified CC corresponding tomographic plane and information on the specified MLO corresponding tomographic plane to the display controller 53. The information on the corresponding tomographic plane is information indicating which of the plurality of tomographic planes TFi is the corresponding tomographic plane, and is, for example, the numerical value of i and a height from the detection surface 22A. Instead of the height from the detection surface 22A, a height from the tomographic plane TF1 may be used.

The display controller 53 performs control to display various screens on the display 34 which is an example of a "display unit" according to the technology of the present disclosure. Specifically, the display controller 53 performs control to display, on the display 34, a transmission instruction acceptance screen 80 (refer to FIG. 13) that accepts a transmission instruction, a selection instruction acceptance screen 95 (refer to FIG. 15) that accepts a selection instruction on at least one image of the CC image or the MLO image, a tomographic image display screen 110 (refer to FIG. 16) on which the tomographic image of the corresponding tomographic plane specified by the specifying unit 52 is displayed, and the like.

Figure 11:
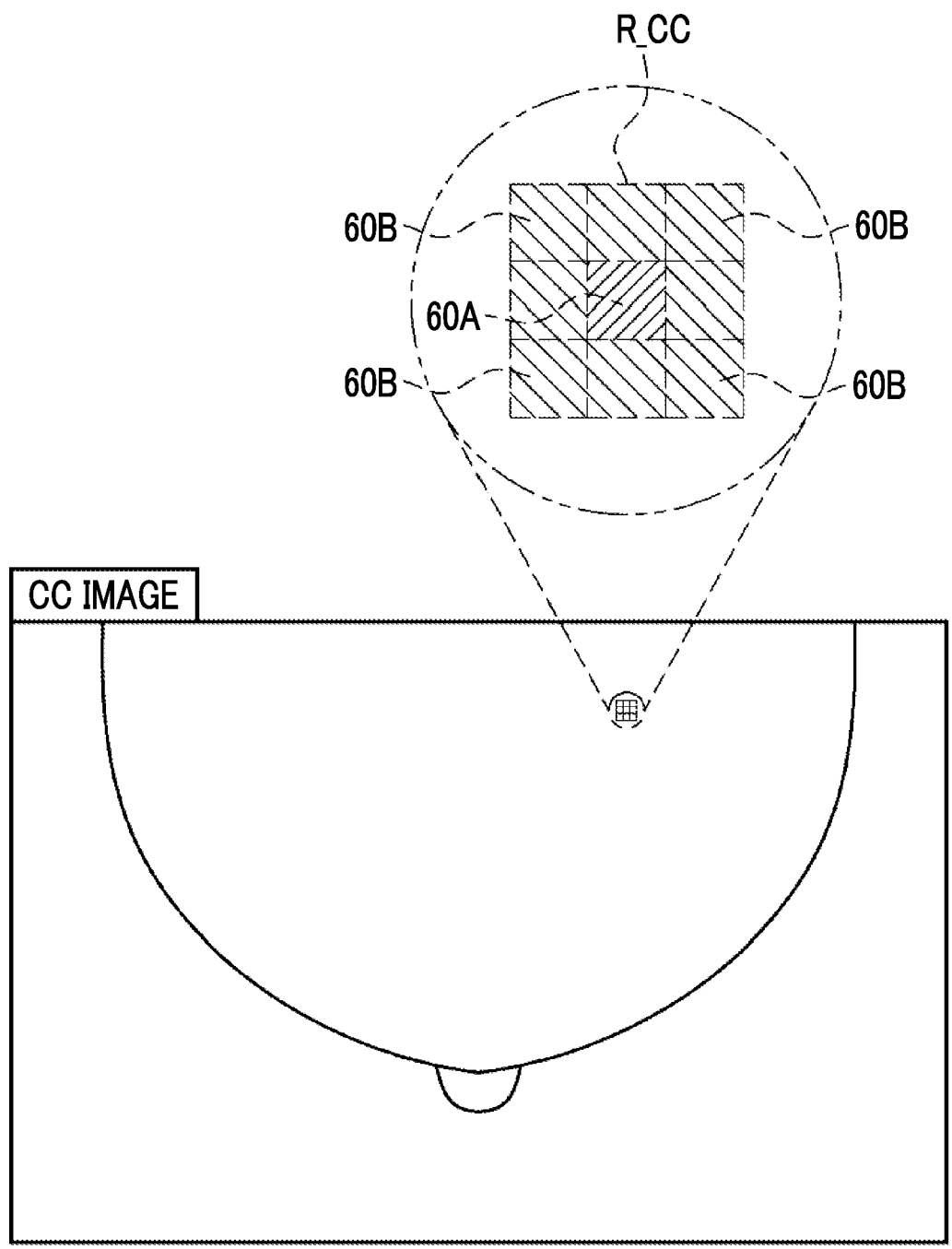
FIG. 11 is a diagram illustrating a region for specifying a corresponding tomographic plane.

As illustrated in FIG. 11, the specifying unit 52 specifies a tomographic plane corresponding to the region R composed of the pixel 60A of the selected location and a plurality of pixels 60B around the pixel 60A of the selected location. Then, the specified tomographic plane corresponding to the region R is specified as the corresponding tomographic plane corresponding to the selected location.

In FIG. 11, a case is exemplified in which the two-dimensional standard image on which the selection instruction is accepted is the CC image and the region R is a square region R_CC composed of a total of nine pixels which are the pixel 60A of the selected location and the eight pixels 60B surrounding the pixel 60A. The method of taking the region R is not limited thereto. The number of pixels constituting the region R may be, for example, 9×9=81 around the pixel 60A. Further, the shape of the region R is not limited to the square, and may be a rectangle, a circle, or an oval.

Figure 12:
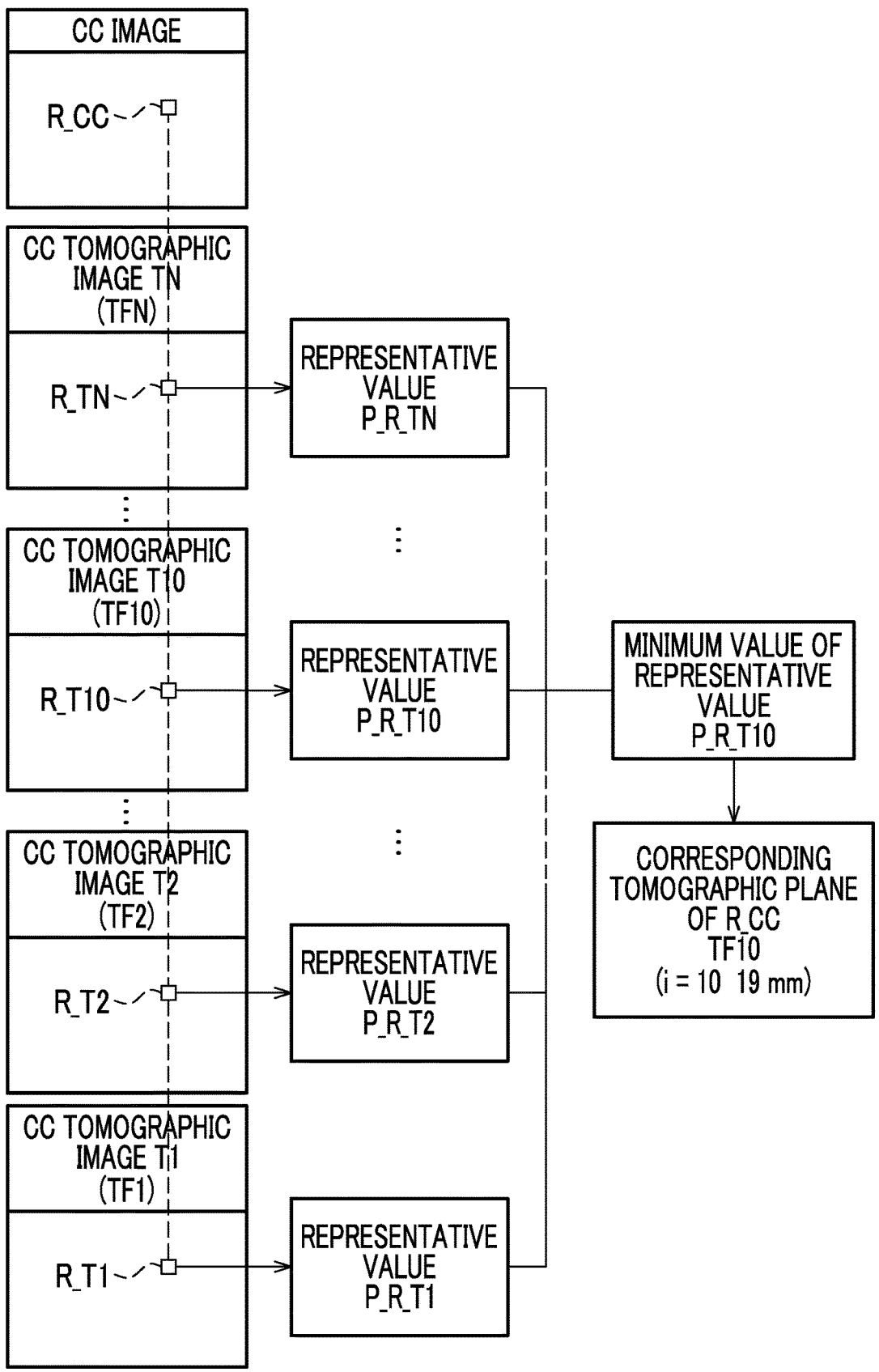
FIG. 12 is a diagram illustrating a state in which the corresponding tomographic plane is specified by a specifying unit.

As illustrated in FIG. 12, the specifying unit 52 obtains a representative value P_R_Ti of the pixel values, for the region R_Ti of each CC tomographic image Ti having a positional relationship corresponding to the region R_CC. The representative value P_R_Ti is an average value, mode, a minimum value, or the like of the pixel values of the region R_Ti, for example.

The specifying unit 52 compares the magnitude of the representative values P_R_Ti, and extracts a minimum value among the representative values P_R_Ti. Then, the tomographic plane TFi of the CC tomographic image Ti having the region R_Ti with the representative value P_R_Ti that is the extracted minimum value, as the corresponding tomographic plane of the region R_CC.

In FIG. 12, a case is exemplified in which the representative value P_R_T10 of the CC tomographic image T10 of the tomographic plane TF10 is the minimum value. In this case, the specifying unit 52 specifies the tomographic plane TF10 as the corresponding tomographic plane of the region R_CC of the CC image. Then, as the information on the corresponding tomographic plane, i=10 and the height 19 mm from the detection surface 22A are output to the display controller 53. Although not illustrated, the specifying unit 52 specifies the corresponding tomographic plane for the region R MLO similar to the region R_CC even in a case where the two-dimensional standard image on which the selection instruction is accepted is the MLO image.

Here, as for the pixel value, a smaller value is assigned to the structure which has a higher absorption coefficient of the radiation 24 and appears whitish in the radiographic image. The selected location is the lesion part such as calcification in many cases, and the lesion part has a relatively high absorption coefficient and has a relatively low pixel value. Accordingly, it can be said that the region R_Ti in which the representative value P_R_Ti is the minimum value is a region in which the probability that the lesion part, that is, the structure of the selected location is present is relatively high. From the above consideration, it can be said that the method of specifying, as the corresponding tomographic plane, the tomographic plane TFi of the CC tomographic image Ti having the region R_Ti in which the representative value P_R_Ti is the minimum value is appropriate as a method of specifying the corresponding tomographic plane. In a case where a higher pixel value is assigned to the structure which has a higher absorption coefficient of the radiation 24, contrary to the above description, the tomographic plane TFi of the CC tomographic image Ti having the region R_Ti in which the representative value P_R_Ti is the maximum value is specified as the corresponding tomographic plane.

The location for specifying the corresponding tomographic plane in the specifying unit 52 may be one pixel 60A instead of the above-described region R. Further, after the corresponding tomographic plane is specified for each of the pixels 60A and 60B constituting the region R, the corresponding tomographic plane of the region R may be specified on the basis of the corresponding tomographic plane of each of the pixels 60A and 60B. Specifically, the average value of the numerical values of i or the heights from the detection surface 22A of the corresponding tomographic planes of the pixels 60A and 60B is obtained, and the tomographic plane indicated by the obtained average value is specified as the corresponding tomographic plane of the region R.

Figure 13:
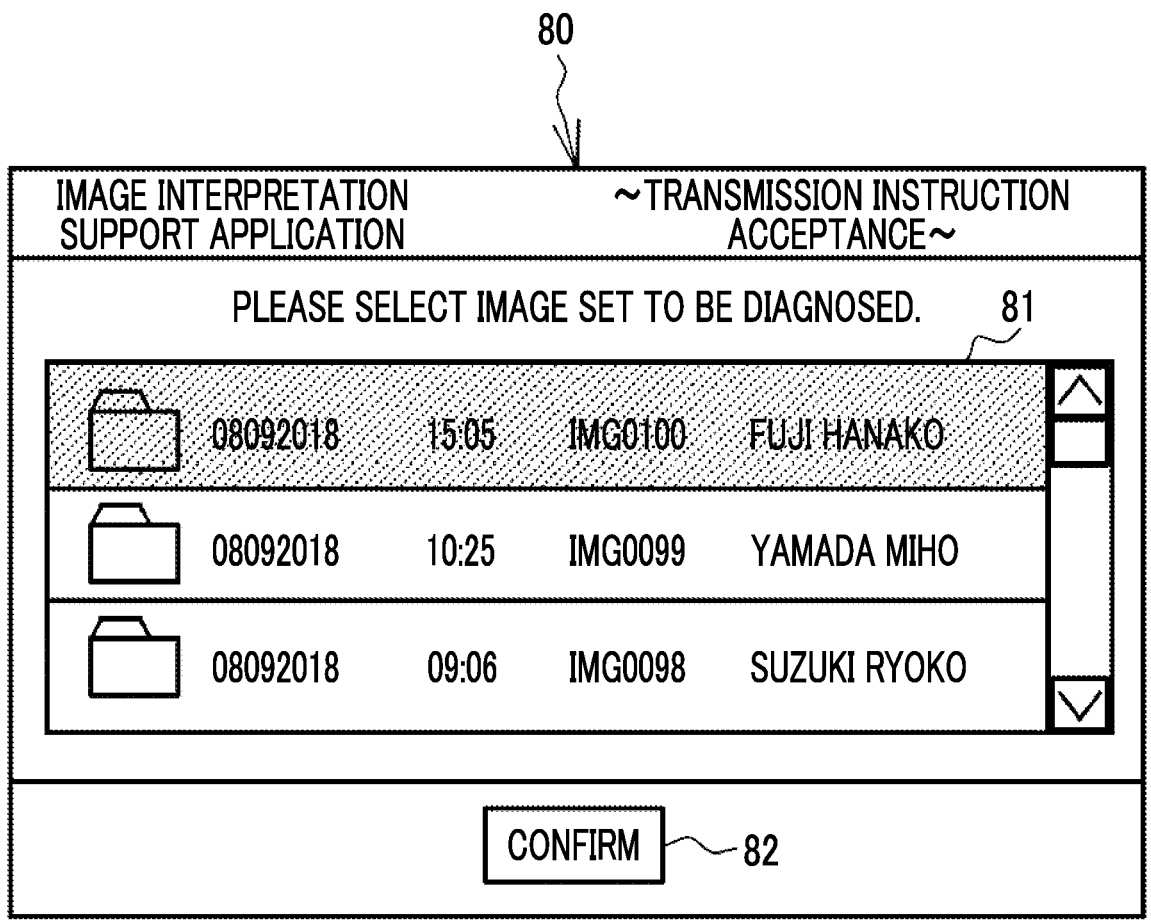
FIG. 13 is a diagram illustrating a transmission instruction acceptance screen.

FIG. 13 illustrates the transmission instruction acceptance screen 80 displayed on the display 34 by the display controller 53. On the transmission instruction acceptance screen 80, an image set display selection region 81 and a confirmation button 82 are provided. In the image set display selection region 81, the image set 27 stored in the PACS server 11 is displayed in a list format so as to be alternatively selectable. In the image set display selection region 81, the imaging date and time, the common image ID, and the patient name of each image set 27 are displayed. The image set 27 selected in the image set display selection region 81 is displayed to be distinguishable from others as illustrated by hatching.

One of the image sets 27 displayed in the image set display selection region 81 is selected, and the confirmation button 82 is selected. In this manner, the transmission instruction of the selected image set 27 is given.

Figure 14:
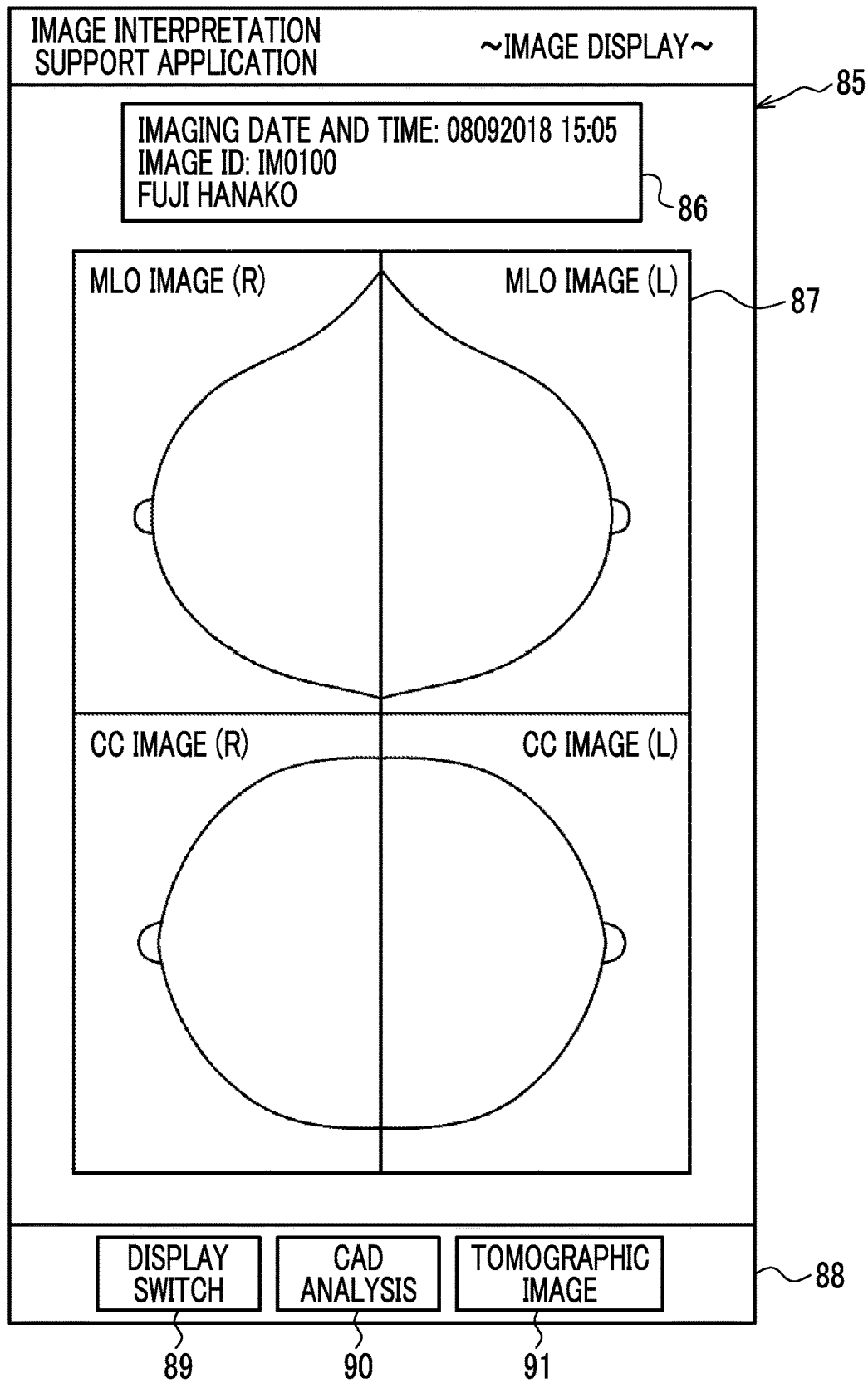
FIG. 14 is a diagram illustrating an image display screen.

FIG. 14 illustrates an image display screen 85. The image display screen 85 is displayed on the display 34 by the display controller 53 instead of the transmission instruction acceptance screen 80 after the transmission instruction is given on the transmission instruction acceptance screen 80. On the image display screen 85, an accessory information display region 86, an image display region 87, and a button display region 88 are provided. In the accessory information display region 86, the imaging date and time, the common image ID, and the patient name are display. In the image display region 87, four images of the MLO image (R), the MLO image (L), the CC image (R), and the CC image (L) are displayed by being arranged vertically and horizontally.

In the button display region 88, a display switch button 89, a computer-aided diagnosis (CAD) analysis button 90, and a tomographic image button 91 are arranged. In a case where the display switch button 89 is selected, the display of the image display region 87 is switched. For example, the illustrated parallel display of four images is switched to a single display of each of four images, a parallel display of the CC image (R) and the CC image (L), and a parallel display of the MLO image (R) and the MLO image (L). In a case where the CAD analysis button 90 is selected, various CAD analyses such as extraction of a lesion part and detection of the type of the structure are performed on the image displayed in the image display region 87. Then, an annotation or the like indicating the analysis result thereof is added to the image displayed in the image display region 87.

The tomographic image button 91 is a button for displaying the tomographic image. In a case where the tomographic image button 91 is selected, the display controller 53 displays the selection instruction acceptance screen 95 displayed in FIG. 15 on the display 34.

Figure 15:
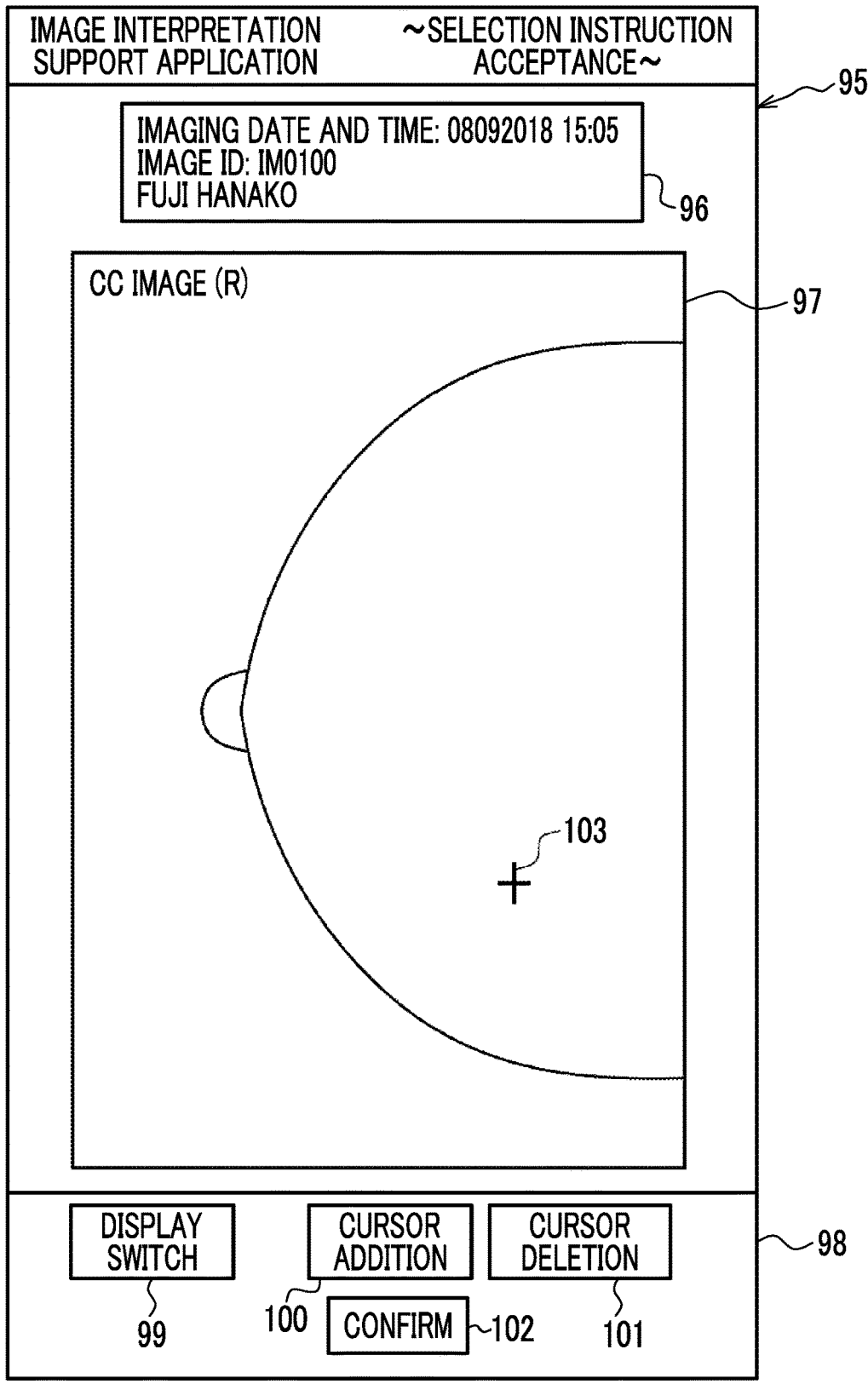
FIG. 15 is a diagram illustrating a selection instruction acceptance screen.

In FIG. 15, in the selection instruction acceptance screen 95, an accessory information display region 96, an image display region 97, and a button display region 98 are provided, as in the image display screen 85 illustrated in FIG. 14. In the button display region 98, a display switch button 99, a cursor addition button 100, a cursor deletion button 101, and a confirmation button 102 are arranged.

In the image display region 97, first, the CC image (R) is displayed. The image to be displayed in the image display region 97 is switched, for example, from the CC image (R) to the CC image (L), the MLO image (R), and further the MLO image (L) by selecting the display switch button 99. In a case where the cursor addition button 100 is selected, one cursor 103 for performing the selection instruction is added to the image display region 97. On the contrary, in a case where the cursor deletion button 101 is selected, the added cursor 103 is deleted from the image display region 97. In this manner, the selection instruction can be performed at a plurality of locations on one image displayed in the image display region 97 by adding the cursor 103.

The cursor 103 can be moved to any location on the image displayed in the image display region 97. In a case where the cursor 103 is moved to a desired location by the user and the confirmation button 102 is selected, the selection instruction is given.

Figure 16:
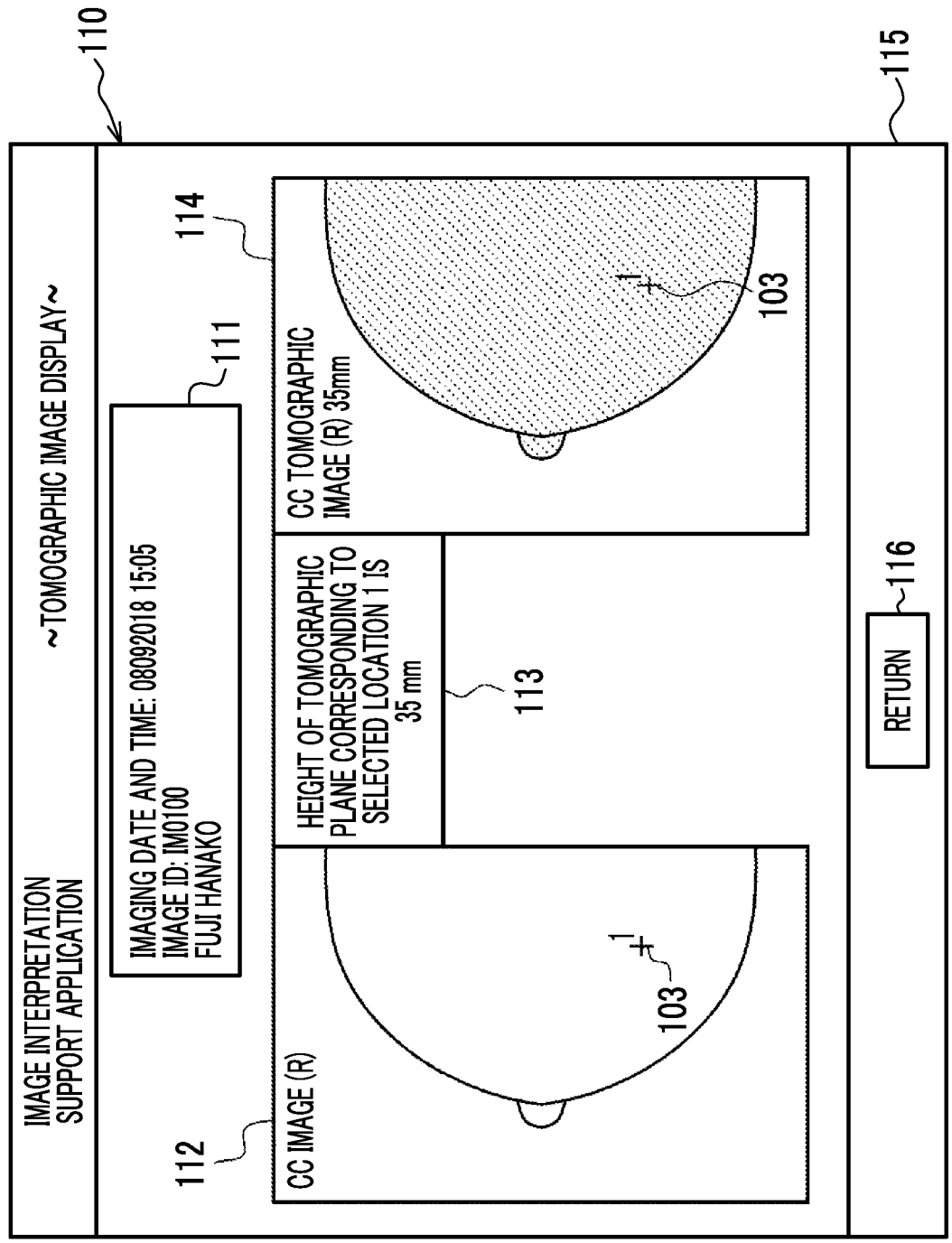
FIG. 16 is a diagram illustrating a tomographic image display screen.

FIG. 16 illustrates the tomographic image display screen 110. The tomographic image display screen 110 is displayed on the display 34 by the display controller 53 instead of the selection instruction acceptance screen 95, after the selection instruction is given in the selection instruction acceptance screen 95. In the tomographic image display screen 110, an accessory information display region 111, a two-dimensional standard image display region 112, a corresponding tomographic plane information display region 113, a tomographic image display region 114, and a button display region 115 are provided.

In the two-dimensional standard image display region 112, the two-dimensional standard image on which the selection instruction is accepted in the selection instruction acceptance screen 95 is displayed. In the corresponding tomographic plane information display region 113, the height of the corresponding tomographic plane is displayed as the information on the corresponding tomographic plane. In the tomographic image display region 114, the tomographic image of the corresponding tomographic plane among the tomographic images obtained by performing the tomosynthesis imaging in the imaging method of the image on which the selection instruction is given is displayed. In each image of the two-dimensional standard image display region 112 and the tomographic image display region 114, the cursor 103 indicating the selected location is displayed with a number indicating a selection order. In FIG. 16, since the image on which the selection instruction is given is the CC image (R) and the height of the corresponding tomographic plane is 35 mm, the CC image (R) is displayed in the two-dimensional standard image display region 112, and the CC tomographic image (R) of which the height of the tomographic plane is 35 mm is displayed in the tomographic image display region 114. Further, in the tomographic image of the corresponding tomographic plane, a scale connecting the upper and lower limit values of the height from the detection surface 22A with a straight line and an arrow indicating the position on the scale of the height of the corresponding tomographic plane from the detection surface 22A may be displayed.

In the button display region 115, a return button 116 is arranged. In a case where the return button 116 is selected, the display returns from the tomographic image display screen 110 to the selection instruction acceptance screen 95.

Figure 17:
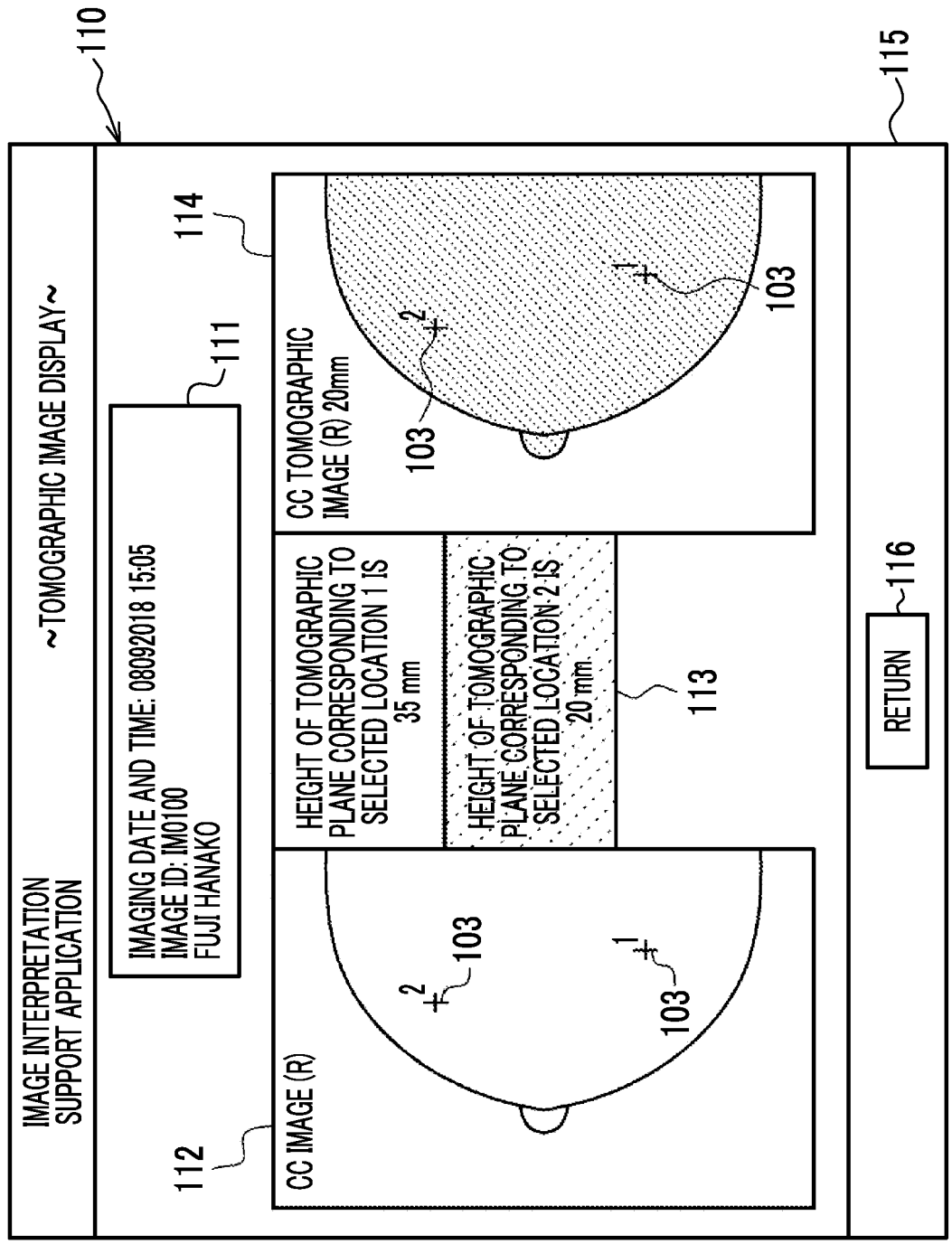
FIG. 17 is a diagram illustrating a tomographic image display screen in a case where there are a plurality of selected locations.

In a case where there are a plurality of selected locations as illustrated in FIG. 17, the display controller 53 displays pieces of information on the corresponding tomographic planes of the respective selected locations in a selectable manner in the corresponding tomographic plane information display region 113. The display controller 53 displays the tomographic image of the corresponding tomographic plane selected in the corresponding tomographic plane information display region 113, in the tomographic image display region 114.

FIG. 17 illustrates a case where information that the height of the corresponding tomographic plane is 20 mm is selected as illustrated by hatching. In this case, in the tomographic image display region 114, the CC tomographic image (R) of which the height of the tomographic plane is 20 mm is displayed.

Figure 18:
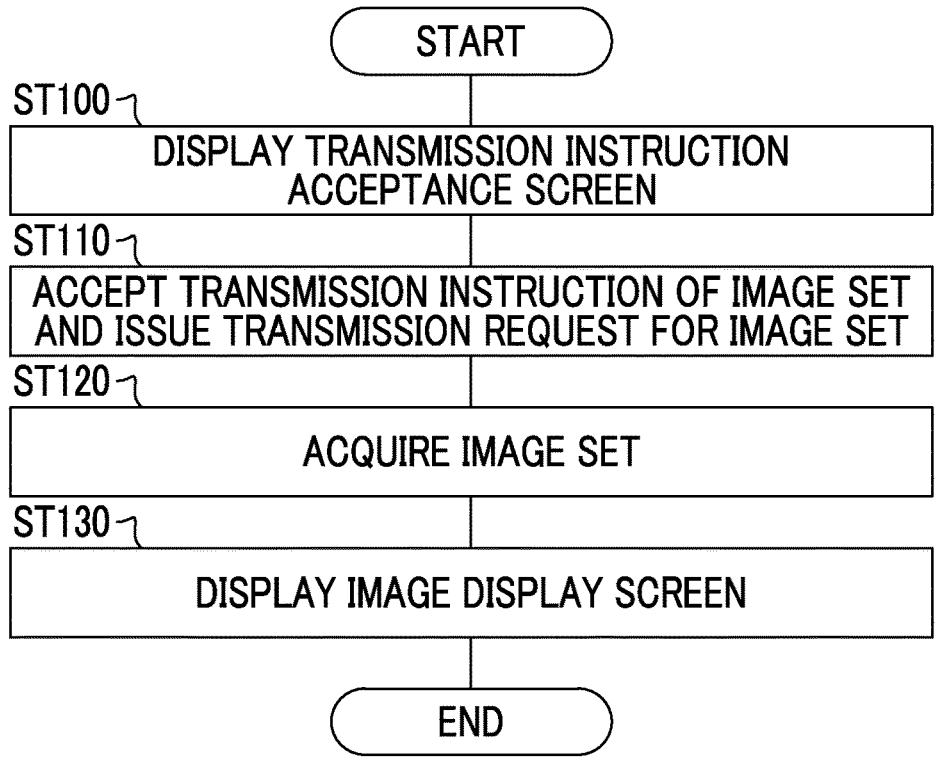
FIG. 18 is a flowchart illustrating a processing procedure of the image interpretation support apparatus.

Next, the operation of the above configuration will be described with reference to the flowcharts illustrated in FIGS. 18 and 19. First, the operation program 40 is activated, and thus the CPU 32 of the computer constituting the image interpretation support apparatus 12 functions as the processing units 50 to 53 as illustrated in FIG. 10. Then, as illustrated in Step ST100 of FIG. 18, the transmission instruction acceptance screen 80 illustrated in FIG. 13 is displayed on the display 34 by the display controller 53.

On the transmission instruction acceptance screen 80, in a case where one image set 27 in the image set display selection region 81 is selected and the confirmation button 82 is selected, the transmission instruction of the image set 27 is accepted by the acceptance unit 50. The transmission instruction is output from the acceptance unit 50 to the acquisition unit 51. In this manner, the transmission request for the image set 27 is issued from the acquisition unit 51 to the PACS server 11 (Step ST110).

Next, the image set 27 that is transmitted from the PACS server 11 in response to the transmission request is acquired by the acquisition unit 51 (Step ST120, acquisition step). The image set 27 is output from the acquisition unit 51 to the specifying unit 52 and the display controller 53. The image display screen 85 illustrated in FIG. 14 is displayed on the display 34 by the display controller 53 on the basis of the image set 27 acquired by the acquisition unit 51 (Step ST130).

Figure 19:
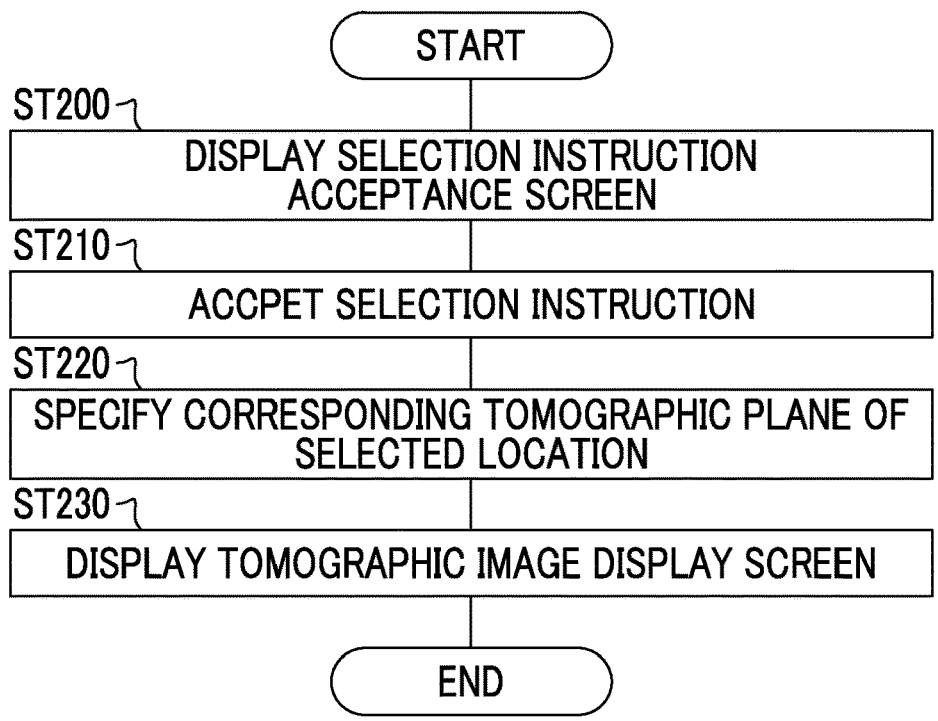
FIG. 19 is a flowchart illustrating a processing procedure of the image interpretation support apparatus.

As illustrated in Step ST200 of FIG. 19, in a case where the tomographic image button 91 is selected on the image display screen 85, the selection instruction acceptance screen 95 illustrated in FIG. 15 is displayed on the display 34 by the display controller 53. On the selection instruction acceptance screen 95, in a case where the cursor 103 is moved to any location on the image displayed in the image display region 97 and the confirmation button 102 is selected, the selection instruction with the location of the cursor 103 as the selected location is accepted by the acceptance unit 50 (Step ST210, acceptance step). The selection instruction is output from the acceptance unit 50 to the specifying unit 52.

In the specifying unit 52, the selection instruction from the acceptance unit 50 is received, and the corresponding tomographic plane corresponding to the selected location is specified as illustrated in FIGS. 11 and 12 (Step ST220, specifying step). More specifically, the tomographic plane corresponding to the region R composed of the pixel 60A of the selected location and the plurality of pixels 60B around the pixel 60A of the selected location is specified as the corresponding tomographic plane corresponding to the selected location.

Here, the size of the lesion part such as calcification which is often selected as the selected location is about 200 μm to 300 μm, and is only a few pixels in the image. Therefore, it is difficult for the user to pinpoint the lesion part such as calcification, and thus the selected location may slightly deviate from the location intended by the user. In this case, the corresponding tomographic plane specified by the specifying unit 52 is completely different from the corresponding tomographic plane of the location originally intended by the user.

Further, quantum noise is scattered in the radiographic image. In a case where the location for specifying the corresponding tomographic plane in the specifying unit 52 is the pixel 60A of the selected location and the quantum noise is scattered in the pixel 60A, the reliability of the specified corresponding tomographic plane is low.

In response to such a problem, in the embodiment, the specifying unit 52 specifies the tomographic plane corresponding to the region R composed of the pixel 60A of the selected location and the plurality of pixels 60B around the pixel 60A, as the corresponding tomographic plane corresponding to the selected location. By doing so, it is possible to prevent the corresponding tomographic plane specified in the specifying unit 52 from being completely different from the corresponding tomographic plane of the location originally intended by the user. In addition, even in a case where the quantum noise is scattered in the pixel 60A, the influence thereof is mitigated by the surrounding pixels 60B, and thus it is possible to secure the reliability of the corresponding tomographic plane.

The information on the corresponding tomographic plane is output from the specifying unit 52 to the display controller 53. Then, the tomographic image display screen 110 illustrated in FIGS. 16 and 17 is displayed on the display 34 by the display controller 53 (Step ST230).

In this manner, in a case where the selection instruction is accepted in the acceptance unit 50, the specifying unit 52 specifies only the corresponding tomographic plane corresponding to the selected location. In the case of the technology in the related art in which the specifying unit 52 specifies the corresponding tomographic plane for each location on the two-dimensional standard image before the selection instruction is accepted in the acceptance unit 50, the processing of specifying the corresponding tomographic plane of a location other than the selected location is useless. However, in the embodiment, it is possible to reduce such useless processing. Further, unlike the technology in the related art, it is not necessary to store the information on the specified corresponding tomographic plane in the storage unit such as the storage device 30, and thus it is possible to reduce the capacity burden on the storage unit.

The display controller 53 performs control to display the tomographic image of the corresponding tomographic plane specified in the specifying unit 52, on the display 34. Accordingly, the tomographic image of the corresponding tomographic plane can be easily provided to the user, and the user can save labor of searching for the tomographic image.

Further, the display controller 53 performs control to display the two-dimensional standard image, in addition to the tomographic image, on the display 34. Accordingly, the user can easily perform image interpretation by comparing the two-dimensional standard image and the tomographic image of the corresponding tomographic plane, and the image interpretation work can proceed smoothly.

Second Embodiment

Figure 20:
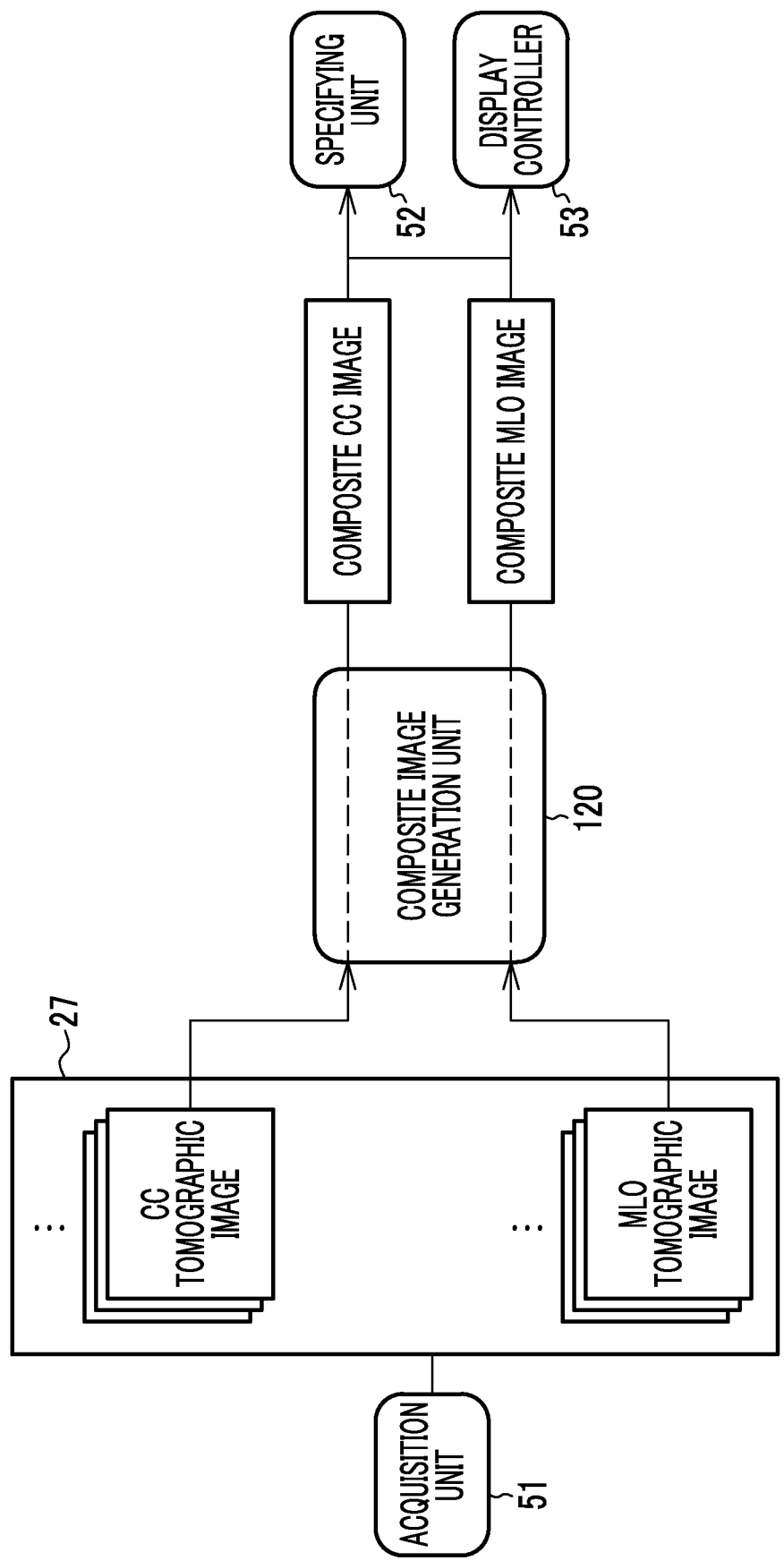
FIG. 20 is a diagram illustrating a second embodiment in which a composite CC image and a composite MLO image are generated to be used as the two-dimensional standard image.
Figure 21:
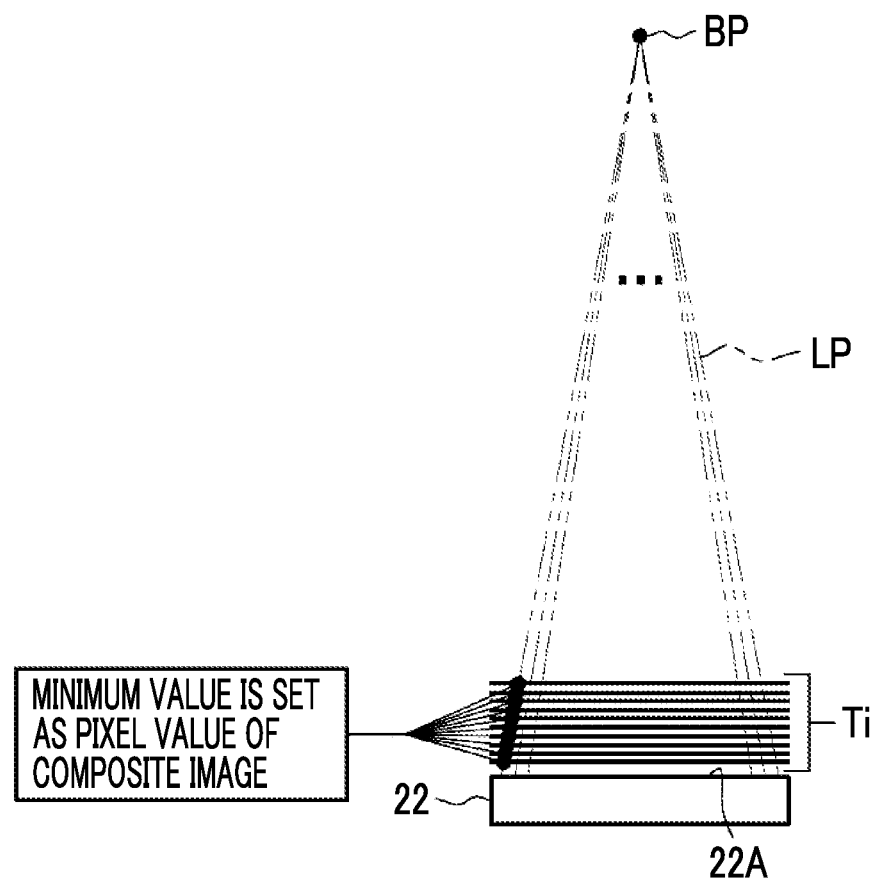
FIG. 21 is a diagram conceptually illustrating a minimum intensity projection method.

In a second embodiment illustrated in FIGS. 20 and 21, a composite craniocaudal view image (composite CC image) is generated on the basis of the plurality of CC tomographic images obtained by the tomosynthesis imaging of the breast 23 in the CC imaging method. Further, a composite mediolateral oblique view image (composite MLO image) is generated on the basis of the plurality of MLO tomographic images obtained by the tomosynthesis imaging of the breast 23 in the MLO imaging method. Then, the composite CC image and the composite MLO image are used as the two-dimensional standard image on which the selection instruction is accepted.

In FIG. 20, a composite image generation unit 120 receives the image set 27 from the acquisition unit 51. The composite image generation unit 120 generates a composite CC image on the basis of the plurality of CC tomographic images by using a well-known composite image generation technology such as a minimum intensity projection method. Similarly, the composite image generation unit 120 generates a composite MLO image on the basis of the plurality of MLO tomographic images by using a well-known composite image generation technology such as a minimum intensity projection method. The composite image generation unit 120 outputs the generated composite CC image and composite MLO image to the specifying unit 52 and the display controller 53.

As conceptually illustrated in FIG. 21, in the minimum intensity projection method, with a generation point of the radiation 24 at the position SP0 illustrated in FIG. 4 as a reference point BP, a projection line LP is drawn from the reference point BP to each location of the detection surface 22A of the radiation detector 22. Then, the minimum value among the pixel values of the locations of the tomographic images Ti through which the projection line LP passes is used as a pixel value of the composite image. In a case where a higher pixel value is assigned to the structure which has a higher absorption coefficient of the radiation 24, a maximum intensity projection method is adopted instead of the minimum intensity projection method.

The specifying unit 52 specifies the corresponding tomographic plane of the selected location of each of the composite CC image and the composite MLO image, instead of the CC image and the MLO image. Further, the display controller 53 displays the composite CC image and the composite MLO image on the image display screen 85 and the selection instruction acceptance screen 95, instead of the CC image and the MLO image. That is, the composite CC image and the composite MLO image are used as the two-dimensional standard image on which the selection instruction is accepted.

In this manner, in the second embodiment, the composite CC image generated on the basis of the plurality of CC tomographic images obtained by the tomosynthesis imaging of the breast 23 in the CC imaging method is used as the two-dimensional standard image. Further, the composite MLO image generated on the basis of the plurality of MLO tomographic images obtained by imaging the breast 23 by the tomosynthesis imaging in the MLO imaging method is used as the two-dimensional standard image. Accordingly, the CC imaging in Step ST10 illustrated in FIG. 6 and the MLO imaging in Step ST20 illustrated in FIG. 7 in the first embodiment are unnecessary, and it is possible to reduce the amount of radiation exposure of the patient. Further, the imaging time can be shortened.

Third Embodiment

In a third embodiment illustrated in FIG. 22, in a case where pixel values of pixels of the region R_Ti are sorted in an ascending order, an average value of the pixel values of the pixels from a preset higher rank to a preset lower rank is used as the representative value P_R_Ti of the pixel values of the pixels of the region R_Ti of the tomographic image Ti having a positional relationship corresponding to the region R_CC.

In FIG. 22, the specifying unit 52 sorts the pixel values of the pixels of the region R_Ti of the tomographic image Ti in an ascending order. Then, the specifying unit 52 obtains an average value of the pixel values of the pixels from a preset higher rank to a preset lower rank, and sets the obtained average value as the representative value P_R_Ti.

FIG. 22 illustrates an example in which the pixel values of the nine pixels of the region R_Ti of the tomographic image Ti are 9, 4, 7, 13, 8, 5, 15, 10, and 12 and an average value (4+5+7+8)/4=6 of the pixel values 4, 5, 7, and 8 of the top four pixels is used as the representative value P_R_Ti. That is, in FIG. 22 the first place is an example of the "preset higher rank" according to the technology of the present disclosure, and the fourth place is an example of the "preset lower rank" according to the technology of the present disclosure.

In this manner, in the third embodiment, in a case where the pixel values of the region R_Ti of the tomographic image Ti are sorted in an ascending order, an average value of the pixel values of the pixels from the preset higher rank to the preset lower rank is used as the representative value P_R_Ti. Accordingly, the robustness against noise can be improved as compared with a case where a specific pixel value such as the minimum value of the pixel values of the region R_Ti is used as the representative value P_R_Ti. The preset higher rank and the preset lower rank are not limited to the first and fourth places exemplified in FIG. 22. The preset higher rank may be the second place, and the preset lower rank may be the fifth place or the like. Further, in a case where a higher pixel value is assigned to the structure which has a higher absorption coefficient of the radiation 24, contrary to the above description, in a case where the pixel values of the pixels of the region R_Ti of the tomographic image Ti are sorted in a descending order, an average value of the pixel values of the pixels from a preset higher rank to a preset lower rank is used as the representative value P_R_Ti.

Fourth Embodiment

In a fourth embodiment illustrated in FIG. 23, the representative value P_R_Ti is obtained after noise removal processing is performed on the region R_Ti of the tomographic image Ti.

In FIG. 23, the specifying unit 52 performs the noise removal processing on the region R_Ti of the tomographic image Ti. The noise removal processing is filter processing using, for example, a smoothing filter, a median filter, or the like. The specifying unit 52 obtains the representative value P_R_Ti of the pixel values of the region R_Ti of the tomographic image Ti after the noise removal processing. Since the method of obtaining the representative value P_R_Ti is the same as that in the third embodiment, the description thereof will be omitted.

FIG. 23 illustrates an example in which the pixel value 0, which is beside the pixel value 10 and below the pixel value 5, is removed by the noise removal processing.

In this manner, in the fourth embodiment, the noise removal processing is performed on the region R_Ti of the tomographic image Ti before the representative value P_R_Ti is obtained. Accordingly, the influence of the noise on the representative value P_R_Ti can be eliminated. FIG. 23 illustrates an example in which the noise removal processing is applied to the third embodiment, but the noise removal processing may be applied to the first embodiment or may be applied to the second embodiment.

The hardware configuration of the computer constituting the image interpretation support apparatus can be variously modified. For example, in order to improve the processing capacity and reliability, the image interpretation support apparatus may be constituted by a plurality of computers that are separated from each other as hardware. Specifically, the functions of the acceptance unit 50 and the acquisition unit 51 and the functions of the specifying unit 52 and the display controller 53 may be distributed in two computers. In this case, the two computers constitute the image interpretation support apparatus.

The operation program 40 is installed in mammography apparatus 10 or the PACS server 11. Then, all or a part of the processing units constructed in the CPU 32 of the image interpretation support apparatus 12 in the embodiments described above may be constructed in the mammography apparatus 10 or the PACS server 11, and the mammography apparatus 10 or the PACS server 11 may be operated as the image interpretation support apparatus 12.

In this manner, the hardware configuration of the computer can be appropriately changed according to the required performance, such as processing capacity, safety, or reliability. Further, in order to secure the safety and the reliability, without being limited to hardware, an application program such as the operation program 40 may be duplicated or may be distributed and stored in a plurality of storage devices.

In the embodiments described above, the PACS server 11 is used in one medical facility, but the PACS server 11 may be used in a plurality of medical facilities. In this case, the PACS server 11 is communicably connected to a plurality of mammography apparatuses 10 and image interpretation support apparatuses 12 installed in a plurality of medical facilities via a wide area network (WAN) such as the Internet or a public communication network. Then, the image of the mammography apparatus 10 in each medical facility and the transmission request from the image interpretation support apparatus 12 in each medical facility are transmitted to the PACS server 11 via the WAN, the image from the mammography apparatus 10 in each medical facility is managed, and the image set 27 is transmitted to the image interpretation support apparatus 12 in each medical facility. In this case, the installation location and management entity of the PACS server 11 may be a data center managed by a company that is different from the medical facility, or may be one of the plurality of medical facilities.

In the embodiments described above, for example, the following various processors can be used as the hardware structure of processing units executing various kinds of processing such as the acceptance unit 50, the acquisition unit 51, the specifying unit 52, the display controller 53, and the composite image generation unit 120. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute specific processing, such as an application specific integrated circuit (ASIC), in addition to the CPU that is a general-purpose processor which executes software (operation program 40) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is a form where one processor is configured by a combination of one or more CPUs and software as typified by a computer, such as a client and a server, and this processor functions as a plurality of processing units. Second, there is a form where a processor realizing the functions of the entire system including a plurality of processing units by one integrated circuit (IC) chip as typified by system on chip (SoC) or the like is used. In this manner, various processing units are configured by using one or more of the above-described various processors as hardware structures.

In addition, specifically, an electric circuit (circuitry) obtained by combining circuit elements, such as semiconductor elements, can be used as the hardware structure of the various processors.

From the above description, the invention described in Additional remark 1 described below can be grasped.

[Additional Remark 1]

An image interpretation support apparatus comprising:
an acquisition processor that acquires a two-dimensional standard image having information on a breast, and a plurality of tomographic images in a plurality of tomographic planes of the breast which are obtained by tomosynthesis imaging of the breast;
an acceptance processor that accepts a selection instruction of a location on the two-dimensional standard image; and
a specifying processor that, in a case where the selection instruction is accepted in the acceptance processor, specifies a corresponding tomographic plane corresponding to a selected location which is the location of which the selection instruction is accepted in the acceptance processor, from among the plurality of tomographic planes on the basis of the plurality of tomographic images.

In the technology of the present disclosure, it is also possible to appropriately combine the above-described various embodiments and various modification examples. Further, without being limited to the embodiments described above, various configurations can be adopted without departing from the scope. Further, in addition to the program, the technology of the present disclosure also extends to a storage medium that stores the program non-temporarily.

The contents described and illustrated above are detailed descriptions of a part relating to the technology of the present disclosure, and are merely examples of the technology of the present disclosure. For example, the above description regarding the configuration, function, action, and effect is a description regarding an example of the configuration, function, action, and effect of a part of the technology of the present disclosure. Accordingly, it goes without saying that with respect to the contents described and illustrated above, unnecessary parts may be deleted, new elements may be added or replaced within a range not departing from the scope of the technology of the present disclosure. In addition, in order to avoid complications and facilitate understanding of a part relating to the technology of the present disclosure, in the contents described and illustrated above, descriptions regarding common technical knowledge and the like that do not require any explanation to enable the implementation of the technology of the present disclosure are omitted.

All documents, patent applications, and technical standards disclosed in this specification are incorporated in this specification by reference to the same extent as if the documents, the patent applications, and the technical standards were specifically and individually stated to be incorporated by reference.

What is claimed is:

1. An image interpretation support apparatus comprising:
an acquisition unit that acquires a two-dimensional standard image having information on a breast, and a plurality of tomographic images in a plurality of tomographic planes of the breast which are obtained by tomosynthesis imaging of the breast;
an acceptance unit that accepts a selection instruction of a location on the two-dimensional standard image; and
a specifying unit that, in a case where the selection instruction is accepted in the acceptance unit, specifies a corresponding tomographic plane corresponding to a selected location which is the location of which the selection instruction is accepted in the acceptance unit, from among the plurality of tomographic planes on the basis of the plurality of tomographic images;

wherein the specifying unit specifies the tomographic plane corresponding to a region composed of a pixel of the selected location and a plurality of pixels around the pixel of the selected location, as the corresponding tomographic plane corresponding to the selected location;

wherein the specifying unit obtains a representative value of pixel values of a region of the tomographic image having a positional relationship corresponding to the region, and specifies the corresponding tomographic plane on the basis of the representative value; and wherein in a case where the pixel values of the pixels of the region of the tomographic image are sorted in an ascending order, the representative value is an average value of the pixel values of the pixels from a preset higher rank to a preset lower rank, or in a case where the pixel values of the pixels of the region of the tomographic image are sorted in a descending order, the representative value is an average value of the pixel values of the pixels from a preset higher rank to a preset lower rank.

2. The image interpretation support apparatus according to claim 1, further comprising:
a display controller that performs control to display the tomographic image of the corresponding tomographic plane specified in the specifying unit, on a display unit.

3. The image interpretation support apparatus according to claim 2,
wherein the display controller performs control to display the two-dimensional standard image on the display unit, in addition to the tomographic image of the corresponding tomographic plane specified in the specifying unit.

4. The image interpretation support apparatus according to claim 1,
wherein the specifying unit obtains the representative value after noise removal processing is performed on the region of the tomographic image.

5. The image interpretation support apparatus according to claim 1,
wherein the two-dimensional standard image is at least one of
a craniocaudal view image obtained by imaging the breast in a craniocaudal direction,
a mediolateral oblique view image obtained by imaging the breast in a mediolateral oblique direction,
a composite craniocaudal view image generated on the basis of a plurality of craniocaudal view tomographic images obtained by the tomosynthesis imaging of the breast in a craniocaudal view imaging method, or
a composite mediolateral oblique view image generated on the basis of a plurality of mediolateral oblique view tomographic images obtained by the tomosynthesis imaging of the breast in a mediolateral oblique view imaging method.

6. A non-transitory computer-readable storage medium storing an operation program of an image interpretation support apparatus which causes a computer to function as:
an acquisition unit that acquires a two-dimensional standard image having information on a breast, and a plurality of tomographic images in a plurality of tomographic planes of the breast which are obtained by tomosynthesis imaging of the breast;
an acceptance unit that accepts a selection instruction of a location on the two-dimensional standard image; and
a specifying unit that, in a case where the selection instruction is accepted in the acceptance unit, specifies a corresponding tomographic plane corresponding to a selected location which is the location of which the selection instruction is accepted in the acceptance unit, from among the plurality of tomographic planes on the basis of the plurality of tomographic images;
wherein the specifying unit specifies the tomographic plane corresponding to a region composed of a pixel of the selected location and a plurality of pixels around the pixel of the selected location, as the corresponding tomographic plane corresponding to the selected location;
wherein the specifying unit obtains a representative value of pixel values of a region of the tomographic image having a positional relationship corresponding to the region, and specifies the corresponding tomographic plane on the basis of the representative value; and
wherein in a case where the pixel values of the pixels of the region of the tomographic image are sorted in an ascending order, the representative value is an average value of the pixel values of the pixels from a preset higher rank to a preset lower rank, or in a case where the pixel values of the pixels of the region of the tomographic image are sorted in a descending order, the representative value is an average value of the pixel values of the pixels from a preset higher rank to a preset lower rank.

7. An operation method of an image interpretation support apparatus, the operation method comprising:
acquiring a two-dimensional standard image having information on a breast, and a plurality of tomographic images in a plurality of tomographic planes of the breast which are obtained by tomosynthesis imaging of the breast;
accepting a selection instruction of a location on the two-dimensional standard image; and
in a case where the selection instruction is accepted specifying a corresponding tomographic plane corresponding to a selected location which is the location of which the selection instruction is accepted from among the plurality of tomographic planes on the basis of the plurality of tomographic images;
wherein the tomographic plane corresponding to a region composed of a pixel of the selected location and a plurality of pixels around the pixel of the selected location is specified as the corresponding tomographic plane corresponding to the selected location;
wherein a representative value of pixel values of a region of the tomographic image having a positional relationship corresponding to the region is obtained, and the corresponding tomographic plane is specified on the basis of the representative value; and
wherein in a case where the pixel values of the pixels of the region of the tomographic image are sorted in an ascending order, the representative value is an average value of the pixel values of the pixels from a preset higher rank to a preset lower rank, or in a case where the pixel values of the pixels of the region of the tomographic image are sorted in a descending order, the representative value is an average value of the pixel values of the pixels from a preset higher rank to a preset lower rank.

* * * * *